(12) United States Patent
Turcott

(10) Patent No.: US 7,738,935 B1
(45) Date of Patent: Jun. 15, 2010

(54) METHODS AND DEVICES FOR REDUCTION OF MOTION-INDUCED NOISE IN PULSE OXIMETRY

(75) Inventor: Robert G. Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1219 days.

(21) Appl. No.: 11/301,709

(22) Filed: Dec. 12, 2005

Related U.S. Application Data

(63) Continuation-in-part of application No. 10/192,368, filed on Jul. 9, 2002, now Pat. No. 6,997,879.

(51) Int. Cl.
*A61B 5/1455* (2006.01)

(52) U.S. Cl. .................................................. 600/336
(58) Field of Classification Search ................. 600/322, 600/323, 331, 336; 702/189, 191
See application file for complete search history.

(56) References Cited

U.S. PATENT DOCUMENTS

| | | | |
|---|---|---|---|
| 3,139,086 A | 6/1964 | Botsch et al. | 128/2.05 |
| 3,412,729 A | 11/1968 | Smith, Jr. | 128/2.05 |
| 4,030,485 A | 6/1977 | Warner | 128/2.05 |
| 4,157,708 A | 6/1979 | Imura | 128/666 |
| 4,266,554 A | 5/1981 | Hamaguri | 600/323 |
| 4,407,290 A | 10/1983 | Wilber | 128/633 |
| 4,418,700 A | 12/1983 | Warner | 128/694 |
| 4,541,439 A | 9/1985 | Hon | 600/504 |
| 4,621,643 A | 11/1986 | New, Jr. et al. | 128/633 |
| 4,653,498 A | 3/1987 | New, Jr. et al. | 128/633 |
| 4,714,080 A | 12/1987 | Edgar et al. | 600/330 |
| 4,714,341 A | 12/1987 | Hamaguri et al. | 356/41 |
| 4,730,389 A | 3/1988 | Baudino et al. | 29/825 |
| 4,750,495 A | 6/1988 | Moore et al. | 128/664 |

(Continued)

FOREIGN PATENT DOCUMENTS

EP       0 524 083 A1       7/1992

(Continued)

OTHER PUBLICATIONS

Yoshiya, et al.; "Spectrophotometric Monitoring of Arterial Oxygen Saturation in the Fingertip"; Medical & Biological Engineering & Computing; Jan. 1980; pp. 27-32.

(Continued)

*Primary Examiner*—Eric F Winakur
*Assistant Examiner*—Etsub D Berhanu
(74) *Attorney, Agent, or Firm*—Steven M. Mitchell

(57) ABSTRACT

Methods and devices are provided for reducing motion artifacts when measuring blood oxygen saturation. A portion of the light having the first wavelength, a portion of light having the second wavelength and a portion of the light having the third wavelength are received. A first signal is produced based on the received portion of light having the first wavelength. Similarly, a second signal is produced based on the received portion of light having the second wavelength, and a third signal is produced based on the received portion of light having the third wavelength. A difference between the second signal and the first signal is determined, wherein the difference signal is first plethysmography signal. Similarly, a difference is determined between the third signal and the first signal to produce a second plethysmography signal. Blood oxygen saturation is then estimated using the first and second plethysmography signals.

33 Claims, 12 Drawing Sheets

U.S. PATENT DOCUMENTS

| | | | | |
|---|---|---|---|---|
| 4,815,469 A | 3/1989 | Cohen et al. | | 128/634 |
| 4,819,752 A | 4/1989 | Zelin | | 128/633 |
| 4,832,484 A | 5/1989 | Aoyagi et al. | | 356/41 |
| 4,834,107 A | 5/1989 | Warner | | 128/668 |
| 4,907,594 A | 3/1990 | Muz | | 600/335 |
| 5,040,533 A | 8/1991 | Fearnot | | 128/419 |
| 5,040,538 A | 8/1991 | Mortazavi | | 128/633 |
| 5,055,671 A | 10/1991 | Jones | | 250/227.21 |
| 5,112,124 A * | 5/1992 | Harjunmaa et al. | | 356/39 |
| 5,176,137 A | 1/1993 | Erickson et al. | | 128/419 |
| 5,222,495 A | 6/1993 | Clarke et al. | | 128/633 |
| 5,246,002 A | 9/1993 | Prosser | | 600/336 |
| 5,349,961 A | 9/1994 | Stoddart et al. | | 128/665 |
| 5,396,893 A | 3/1995 | Oberg et al. | | 128/671 |
| 5,413,100 A | 5/1995 | Barthelemy et al. | | 128/633 |
| 5,421,329 A | 6/1995 | Casciani et al. | | 128/633 |
| 5,458,117 A * | 10/1995 | Chamoun et al. | | 600/547 |
| 5,490,505 A | 2/1996 | Diab | | 600/323 |
| 5,499,627 A | 3/1996 | Steuer et al. | | 128/633 |
| 5,544,661 A | 8/1996 | Davis et al. | | 128/700 |
| 5,556,421 A | 9/1996 | Prutchi et al. | | 607/36 |
| 5,676,141 A | 10/1997 | Hollub | | 128/633 |
| 5,730,125 A | 3/1998 | Prutchi | | 600/323 |
| 5,755,226 A * | 5/1998 | Carim et al. | | 600/323 |
| 5,779,631 A | 7/1998 | Chance | | 600/328 |
| 5,857,975 A | 1/1999 | Golub | | 600/485 |
| 5,862,805 A | 1/1999 | Nitzan | | 128/898 |
| 5,865,755 A | 2/1999 | Golub | | 600/485 |
| 5,891,022 A | 4/1999 | Pologe | | 600/323 |
| 5,954,644 A | 9/1999 | Dettling et al. | | 600/322 |
| 6,018,673 A | 1/2000 | Chin et al. | | 600/322 |
| 6,064,898 A | 5/2000 | Aldrich | | 600/316 |
| 6,104,938 A | 8/2000 | Huiku et al. | | 600/322 |
| 6,122,536 A | 9/2000 | Sun et al. | | 600/341 |
| 6,151,516 A | 11/2000 | Kiani-Azarbayjany | | 600/322 |
| 6,374,129 B1 | 4/2002 | Chin et al. | | 600/322 |
| 6,393,311 B1 | 5/2002 | Edgar et al. | | 600/323 |
| 6,594,513 B1 * | 7/2003 | Jobsis et al. | | 600/328 |
| 2001/0047128 A1 * | 11/2001 | Benni | | 600/323 |
| 2002/0077536 A1 * | 6/2002 | Diab et al. | | 600/323 |
| 2002/0111546 A1 * | 8/2002 | Cook et al. | | 600/322 |
| 2002/0177762 A1 * | 11/2002 | Norris et al. | | 600/323 |
| 2006/0247506 A1 * | 11/2006 | Balberg et al. | | 600/323 |

FOREIGN PATENT DOCUMENTS

WO  WO 94/03102  2/1994

OTHER PUBLICATIONS

Flewelling; "Noninvasive Optical Monitoring"; Biomedical Engineering Handbook; CRC Press, Inc., 1995; pp. 1346-1356.

Coetzee, et al.,"Noise-Resistant Pulse Oximetry Using a Synthetic Reference Signal", IEEE Transactions on Biomedical Engineering, vol. 47, No. 8, Aug. 2000, pp. 1018-1026.

* cited by examiner

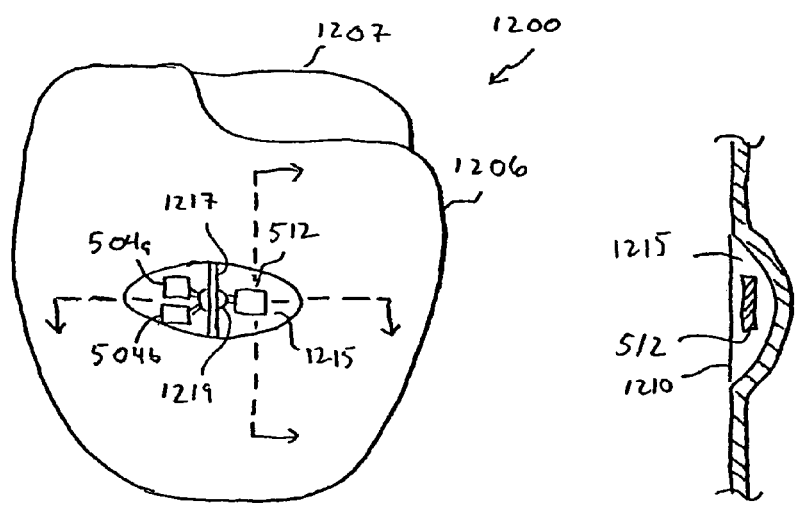
FIG 12c
FIG 12a
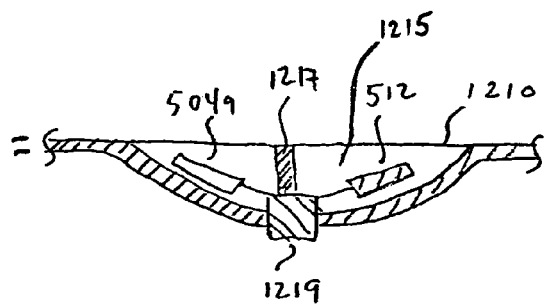
FIG 12b

METHODS AND DEVICES FOR REDUCTION OF MOTION-INDUCED NOISE IN PULSE OXIMETRY

REFERENCE TO RELATED APPLICATIONS

This application is a continuation-in-part of U.S. patent application Ser. No. 10/192,368, filed, Jul. 9, 2002 now U.S. Pat. No. 6,997,879, entitled "Methods and Devices for Reduction of Motion-Induced Noise in Optical Vascular Plethysmography," which is incorporated herein by reference in its entirety.

BACKGROUND OF THE INVENTION

1. Field of the Invention

The present invention relates generally to methods and devices for measuring oxygen saturation of a patient's blood, and more particularly to methods and devices for performing pulse oximetry.

2. Related Art

Plethysmography is a generic term referring to a variety of techniques for monitoring volume changes, for example, volume changes of the lungs due to respiration, or of blood vessels of a limb or tissue segment. When applied to measurements of blood volume, changes occur in a pulsatile manner with each beat of the heart as blood flows in and out of a portion of the body. The study of vascular activity by fluid displacement methods dates back to at least 1890. More contemporary techniques include strain gauge, pneumatic, impedance, doppler, and photoelectric plethysmography. A plethysmography device produces a waveform that is similar to an arterial pressure waveform. The waveform is useful in measuring pulse velocity and indicating arterial obstructions.

FIG. 1 illustrates an exemplary plethysmograph 100, which includes a waveform 102 produced by a plethysmography device. For timing reference, an electrocardiogram (ECG) signal 104 is illustrated. Waveform 102 provides a measure of the volume of the arterial vasculature. A measure of arterial pulse amplitude is derived from it. A few tens to a few hundreds of milliseconds after the QRS complex, the plethysmography voltage reaches a minimum and starts to increase. This is due to the increasing blood volume in the arterioles as the systolic pulse reaches the periphery. The delay is influenced by the distance that the sensor is placed from the heart. It requires approximately 100 msec for the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

A photoplethysmography device (PPG) (also called a pseudoplethysmography or photoelectric plethysmography device) includes a light detector and a light source. The PPG utilizes the transmission or reflection of light to demonstrate the changes in blood perfusion. Such devices might be used in the cardiology department or intensive care department of a hospital or in a clinic for diagnostic purposes related to vascular surgery. A photoplethysmography device is also referred to, herein, simply as a plethysmography device.

An exemplary circuit 200A for a conventional photoplethysmography device is shown in FIG. 2A. An exemplary mechanical arrangement 200B for a conventional photoplethysmography device is shown in FIG. 2B. In these examples, the light source includes a light-emitting diode (LED) 202, although in alternative models an incandescent lamp can be used. The light detector in this example includes a photoresistor 204 excited by a constant current source. Changes in light intensity cause proportional changes in the resistance of photoresistor 204. Since the current through photoresistor 204 is constant in this example, the resistance changes produce varying analog voltage ($V_{out\_analog}$) at the output terminal. This varying analog voltage ($V_{out\_analog}$) is typically converted to a digital signal ($V_{out\_digital}$) using an analog to digital converter (A/D) 206. Other known light detectors include photo diodes, photo transistors, photo darlingtons and avalanche photo diodes.

Light may be transmitted through a capillary bed such as in an ear lobe or finger tip. As arterial pulsations fill the capillary bed the changes in volume of the blood vessels modify the absorption, reflection and scattering of the light. Stated another way, an arterial pulse in, for example, a finger tip, or ear lobe, causes blood volume to change, thereby changing the optical density of the tissue. Therefore, the arterial pulse modulates the intensity of the light passing through the tissue. Light from LED 202 is reflected into photoresistor 204 by scattering and/or by direct reflection from an underlying bone structure. Such a PPG does not indicate "calibratable" value changes. Thus, its usefulness is generally limited to pulse-velocity measurements, determination of heart rate, and an indication of the existence of a pulse (e.g., in a finger). Additionally, a conventional PPG provides a poor measure of changes in volume and is very sensitive to motion artifacts.

It is noted that photoplethysmography devices may operate in either a transmission configuration or a reflection configuration. In the transmission configuration, LED 202 and the photodetector 204 face one another and a segment of the body (e.g., a finger or earlobe) is interposed between them. In the reflection configuration, LED 202 and photodetector 204 are mounted adjacent to one another, e.g., on the surface of the body, as shown in FIG. 2B.

Pulse oximetry combines the principles of optical plethysmography and spectrophotometry to determine arterial oxygen saturation values. Optical plethysmography, as just explained above, uses light absorbance technology to reproduce waveforms produced by pulsating blood. Spectrophotometry uses various wavelengths of light to perform quantitative measurements about light absorption through given substances. Using these two principles, the arterial oxygen saturation of a patient's blood can be estimated. Arterial oxygen saturation measurements can be used, for example, to monitor and assess heart failure, sleep apnea, and pulmonary function.

Conventional two wavelength pulse oximeters (which perform pulse oximetry) emit light from two LEDs into a pulsatile tissue bed and collect the transmitted light with a photodetector positioned on an opposite surface (transmission pulse oximetry), or an adjacent surface (reflectance pulse oximetry). The "pulse" in pulse oximetry comes from the time varying amount of arterial blood in the tissue during the cardiac cycle, and the processed signals from the photodetector create the familiar plethysmographic waveform due to the cycling light attenuation. For estimating oxygen saturation, at least one of the two LEDs' primary wavelength is chosen at some point in the electromagnetic spectrum where the absorption of oxyhemoglobin ($HbO_2$) differs from the absorption of reduced hemoglobin (Hb). The second of the two LEDs' wavelength must be at a different point in the spectrum where, additionally, the absorption differences between Hb and $HbO_2$ are different from those at the first wavelength. Commercial pulse oximeters typically utilize one wavelength in the red part of the visible spectrum near 660 nanometers (nm), and one in the near infrared part of the spectrum in the range of 880 nm-940 nm. Photocurrents generated within the photodetector are detected and processed for measuring the modulation ratio of the red to infrared signals. This modulation ratio has been observed to correlate well to arterial oxygen saturation. Pulse oximeters are empirically calibrated by measuring the modulation ratio over a range of in vivo measured arterial oxygen saturations ($SaO_2$) on a set of patients, healthy volunteers, or animals. The observed correlation is used in an inverse manner to estimate saturation ($SpO_2$) based on the real-time measured value of modulation ratios. (As used herein, $SaO_2$ refers to the in vivo measured functional saturation, while $SpO_2$ is the estimated functional saturation using pulse oximetry.)

A pulse oximeter resembles the plethysmography device shown in FIG. 2B, except two LEDs (e.g., a red (660 nm) LED and an infrared (940 nm) LED) are used to transmit light through a vascular bed to the photodetector. The difference in the intensity of transmitted light between red and infrared light is caused by the differences in the absorption of light by oxygenated (saturated) and deoxygenated (desaturated) hemoglobin. The resulting voltage difference is used to estimate the amount of oxygen saturation by, for example, comparing the voltage difference to a table.

A problem with current methods and devices for performing pulse oximetry is that they are acutely sensitive to sensor and/or tissue motion. Even rather subtle motion can (and often do) swamp the detected optical signals and render the oxygen saturation measurements unusable. For example, with pulse oximetry devices that measure blood volume changes in a fingertip or earlobe, such subtle motion may be caused by a patient's slight movement of their finger or head. Accordingly, there is a need to reduce motion-induced noise in pulse oximetry.

SUMMARY OF THE INVENTION

Embodiments of the present invention relate to methods and devices for reducing effects of motion when measuring blood oxygen saturation.

Light having a first wavelength, light having a second wavelength and light having a third wavelength are transmitted through body tissue. This can be accomplished by transmitting the light through a human appendage, toward the epidermis of a patient, or through tissue within the body of a patient.

A portion of the light having the first wavelength, a portion of the light having the second wavelength and a portion of the light having the third wavelength are received. A first signal is produced based on the received portion of light having the first wavelength. Similarly, a second signal is produced based on the received portion of light having the second wavelength, and a third signal is produced based on the received portion of light having the third wavelength. A difference between the second signal and the first signal is determined, wherein the difference signal is a first plethysmography signal. Similarly, a difference is determined between the third signal and the first signal to produce a second plethysmography signal. Blood oxygen saturation is then estimated using the first and second plethysmography signals. In accordance with embodiments of the present invention, an average of the second signal and an average of the third signal (and possibly an average of the first signal) are determined and used when estimating the blood oxygen saturation. More specifically, these signals are used to determine a statistic, which in turn is used to estimate the blood oxygen saturation. Beneficially, the effects of motion artifacts on the statistic (that can be calculated in accordance with various embodiments of the present invention) are reduced (and preferably minimized), thereby increasing the accuracy of blood oxygen saturation estimates.

In accordance with an embodiment of the present invention, a first ratio between an intensity of the light having the first wavelength and an intensity of the light having the second wavelength is adjusted to reduce motion artifacts. Similarly, a second ratio between an intensity of the light having the first wavelength and an intensity of the light having the third wavelength is adjusted to reduce motion artifacts. This can be accomplished, for example, by keeping an intensity of the light having the first wavelength constant while the intensity of the light having the second wavelength is adjusted to substantially minimize the motion artifacts associated with the first plethysmography signal, and the intensity of the light having the third wavelength is adjusted to substantially minimize motion artifacts associated with the second plethysmography signal. Stated more generally, intensities of the light having the first wavelength, the light having the second wavelength, and the light having the third wavelengths are selected to substantially minimize motion artifacts in the first plethysmography signal and in the second plethysmography.

In an alternative embodiment of the present invention, a first ratio between a gain of the first signal and a gain of the second signal is adjusted to reduce motion artifacts. Similarly, a second ratio between a gain of the first signal and a gain of the third signal is adjusted to reduce motion artifacts. This can be accomplished, for example, by keeping a gain of the first signal constant while the gain of the second signal is adjusted to substantially minimize motion artifacts associated with the first plethysmography signal, and the gain of the third signal is adjusted to substantially minimize motion artifacts associated with the second plethysmography signal.

In accordance with a specific embodiment of the present invention, the first wavelength is about 805 nm, the second wavelength is about 660 nm and the third wavelength is about 905 nm.

Devices for measuring blood oxygen saturation, in accordance with embodiments of the present invention include a light source, a light detector, a pair of comparators, and a processor. The light source and light detector can be arranged with respect to one another in a transmission or reflective configuration. The light source transmits light having a first wavelength, light having a second wavelength and light having a third wavelength through body tissue. The light detector receives a portion of the light having the first wavelength, a portion of the light having the second wavelength, and a portion of the light having the third wavelength. The light detector produces a first signal, based on the received portion of light having the first wavelength, a second signal, based on the received portion of light having the second wavelength, and a third signal, based on the received portion of the light having the third wavelength. A first comparator subtracts one of the first and second signals from the other to produce a first plethysmography signal. Similarly, a second comparator subtracts one of the first and third signals from the other to produce a second plethysmography signal. The processor, or other equivalent device, then estimates the blood oxygen saturation using the first and second plethysmography signals. The processor may also use averages of the second and third signal (and possible an average of the first signal) when determining an estimate of the blood oxygen saturation, as is explained below in more detail.

The light source can include multiple light emitting diodes to produce the light having the first wavelength, the light having the second wavelength and the light having the third wavelength. Alternatively, lasers or laser-diodes can be used to produce light at specific wavelengths. The light source can alternatively be a broad-spectrum source such as an incandescent lamp or a tungsten halogen lamp. With a broad spectrum source, frequency selective optical filters are used to provide signals corresponding to each wavelength.

The light detector can include a single photodetector (also known as a photocell), or multiple photodetectors, to receive the portion of the light having the first wavelength, the portion of light having the second wavelength and the portion of light having the third wavelength.

In non-implantable embodiments, the transmitted light can be transmitted, for example, through a patient's finger, earlobe, foot or hand. The light can also be applied to the epidermis of a patient at various other locations about a patient's body. In implantable embodiments of the present invention, the light source and the light detector are incorporated into an implantable housing and the light having a first wavelength, the light having the second wavelength, and the light having the third wavelength are transmitted toward tissue within the patient's body.

Further features and advantages of the present invention may be more readily understood by reference to the following description taken in conjunction with the accompanying drawings and claims.

BRIEF DESCRIPTION OF THE DRAWINGS/FIGURES

The left-most digit(s) of a reference number identifies the drawing in which the reference number first appears.

FIG. 12 illustrates an implantable device, according to an embodiment of the present invention;

DETAILED DESCRIPTION OF THE INVENTION

Figure 1:
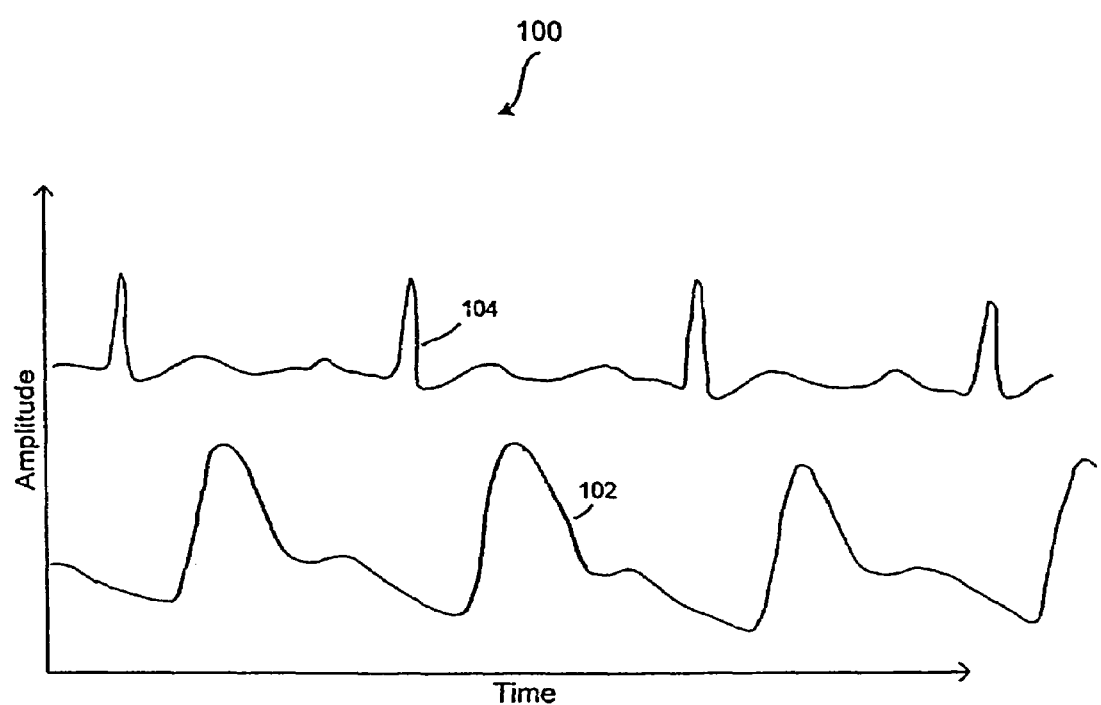
FIG. 1 illustrates an exemplary waveform produced by a plethysmography device.

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

In accordance with an embodiment of the present invention, the requirements on the optical properties of a photoplethysmography system which minimizes noise artifact are defined mathematically using a modified version of the Beer-Lambert law. The Beer-Lambert law relates attenuation of light intensity to the optical pathlength and optical properties of a sample. The absorption coefficients that appear in the Beer-Lambert law are defined under precisely controlled laboratory conditions. In a practical setting, particularly with living biological tissues, the measured absorption of the material may deviate from what is measured in the laboratory. This can occur for a number of reasons, including the effect of scattering on the light path, the geometrical orientation of the light source and detector, and anisotropic nature of the tissue. Furthermore, there are many distinct substances in tissue, each with their own absorption properties. Embodiments of the present invention account for these deviations from the model and incorporate the effect of multiple absorbing constituents by using effective absorption coefficients and effective pathlengths. Furthermore, precise knowledge of the values of effective absorption coefficients and effective pathlengths is not necessary for the function of the invention.

In the modified version of the Beer-Lambert law, let $K_t$ and $K_b$ be the effective absorption coefficients of the non-blood tissue and the blood, respectively, and let $l_t(t)$ and $l_b(t)$ be the effective time-varying optical pathlength of each. In general, motion will influence the effective optical path length of the blood. However, for small perturbations, the change in interstitial pressure due to motion is small relative to the blood pressure, so the effect of motion on the optical pathlength of the blood can be neglected. Thus, the effect of motion is contained in the optical pathlength of the non-blood tissue, $l_t(t)$, while the time-varying vascular volume is contained in the optical pathlength of the blood, $l_b(t)$. The modified version of the Beer-Lambert law predicts that the detected light intensity, I, is related to the effective incident light intensity, $I_0$, by $$I = I_0 \exp(-K_t l_t(t) - K_b l_b(t)).$$

In this adaptation of the Beer-Lambert law, the effective incident light intensity $I_0$ is not the same as the total light intensity generated at the source, most of which is scattered away by the tissue. Rather, it is that fraction of the total intensity that would impinge on the detector had it not been absorbed by the non-blood tissue or blood.

Using subscripts to indicate the intensities and absorption coefficients of two different wavelengths of light, $\lambda_1$ and $\lambda_2$, and taking the difference between the detected signals, we have $$I_1 - I_2 = I_{0,1} \exp(-K_{t1} l_t(t) - K_{b1} l_b(t)) - I_{0,2} \exp(-K_{t2} l_t(t) - K_{b2} l_b(t))$$

Since the products of the absorption coefficients and the optical pathlengths are small compared to unity, we can use the approximation $e^{-x} \cong 1 - x$, so that $$I_1 - I_2 = I_{0,1} - I_{0,2} + l_t(t)(-I_{0,1}K_{t1} + I_{0,2}K_{t2}) + l_b(t)(-I_{0,1}K_{b1} + I_{0,2}K_{b2})$$

$$= I_{0,1} - I_{0,2} + l_t(t)(I_{0,1}K_{t1})\left(\frac{I_{0,2}K_{t2}}{I_{0,1}K_{t1}} - 1\right) +$$

$$l_b(t)(I_{0,1}K_{b1})\left(\frac{I_{0,2}K_{b2}}{I_{0,1}K_{b1}} - 1\right)$$

$$= I_{0,1} - I_{0,2} + l_t(t)(I_{0,1}K_{t1})\left[\left(\frac{I_{0,2}}{I_{0,1}}\right)\left(\frac{K_{t2}}{K_{t1}}\right) - 1\right] +$$

$$l_b(t)(I_{0,1}K_{b1})\left[\left(\frac{I_{0,2}}{I_{0,1}}\right)\left(\frac{K_{b2}}{K_{b_1}}\right) - 1\right]$$

If the intensity of the sources is set so that $r_{opt} \equiv I_{0,2}/I_{0,1} = K_{t1}/K_{t2}$, then the multiplier of $l_t(t)$ becomes zero and the effect of motion is removed from the difference signal. Furthermore, if wavelengths $\lambda_1$ and $\lambda_2$ are chosen such that the ratios of absorption coefficients of tissue and blood are not equal, i.e., $K_{t2}/K_{b2} \neq K_{t1}/K_{b1}$, then the multiplier of the blood pathlength is not zero, and the plethysmography signal is preserved. Under these constraints, the difference signal becomes $$I_1 - I_2 = I_{0,1} - I_{0,2} + l_b(t)(I_{0,1}K_{t1})\left[\left(\frac{I_{0,2}}{I_{0,1}}\right)\left(\frac{K_{b2}}{K_{b1}}\right) - 1\right],$$

which depends entirely on the optical pathlength of the blood, and not on the optical pathlength of the tissue. Thus, the effect of motion on the tissue is removed from the detected signal.

Figure 4A:
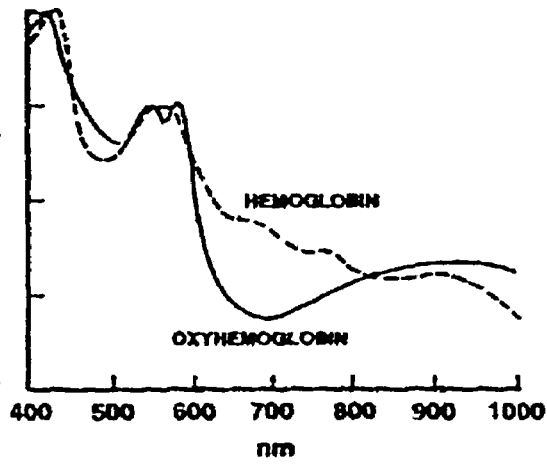
FIGS. 4A-4D shows graphs of absorption spectrum for various blood and non-tissue elements.
Figure 4B:
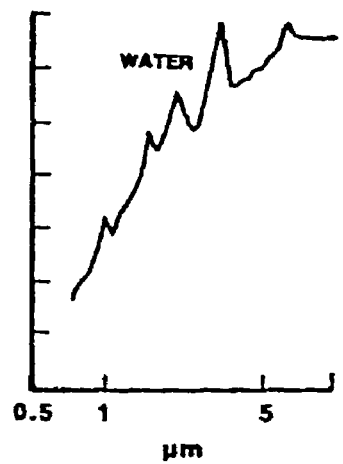
Figure 4C:
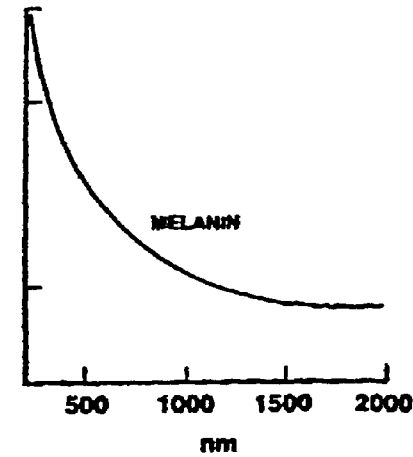

The hemoglobin component of blood strongly absorbs light with wavelengths below around 600 nm, while water is strongly absorbing above around 900 nm. In the range 600-900 nm there is an isobestic point near 805 nm where the absorption of oxygenated hemoglobin (also referred to as oxyhemoglobin) is precisely equal to that of deoxygenated hemoglobin (also simply referred to as hemoglobin). This is shown in a absorption versus wavelength graph shown in FIG. 4A. Setting one wavelength to 805 nm is desirable because it makes the performance of the plethysmograph insensitive to changes in oxygen saturation. In applications such as pulse oximetry, where the photoplethysmograph is used to detect changes in blood oxygen saturation, the isobestic point is not necessarily a desirable wavelength to use.

Figure 4D:
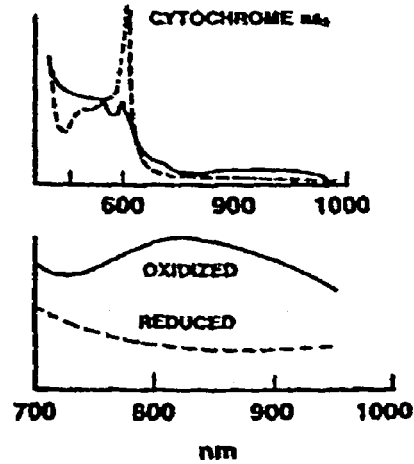

For any two wavelengths that satisfy $K_{t2}/K_{b2} \neq K_{t1}/K_{b1}$, the source intensities $I_{0,1}$ and $I_{0,2}$ can be adjusted to minimize the motion signal while preserving the plethysmography signal. In order to maximize the preserved plethysmography signal, however, the wavelengths should be judiciously chosen so that the difference between $r_1 = K_{t1}/K_{b1}$, and $r_2 = K_{t2}/K_{b2}$ is relatively large. With $\lambda_1$ set near 805 nm (for the reasons described above) this can be achieved by setting $\lambda_2$ near 600 nm, which is the location of a strong absorption peak in another major absorber of light in tissue, cytochrome aa3. This is shown in a absorption versus wavelength graph shown in FIG. 4D.

Like all models of physical and biological systems, the modified Beer-Lambert relation law of the present invention is an approximation. Some deviation from the mathematical prediction is expected, particularly as scattering plays an important role in biological applications. Despite this, the general result will remain true, that is, a ratio of relative intensities $I_{0,2}/I_{0,1}$ can be chosen which preferentially minimizes the effect of motion on the detected signal, while preserving the effect of changing vascular volume.

Because of the potential for deviation from the model, as well as for convenience, it may be desirable to empirically determine the optimal ratio $r_{opt} = I_{0,2}/I_{0,1}$ rather than base it on published values of $K_t$ and $K_b$ and theoretical modeling. This can be done by adjusting the average intensity of one of the sources while applying a controlled mechanical motion to the tissue. In this case, $r_{opt}$ will be taken as the ratio of incident intensities which empirically minimizes the effect of motion in the detected signal.

LEDs are attractive light sources because they produce a narrow range of wavelengths around the nominal value. Furthermore, their operation and the associated control circuitry is simple. Laser diodes and lasers are other possible narrow-spectrum sources. Broad spectrum sources can also be used, with optical filtering performed at the source or detector to provide two effective wavelengths.

Figure 3:
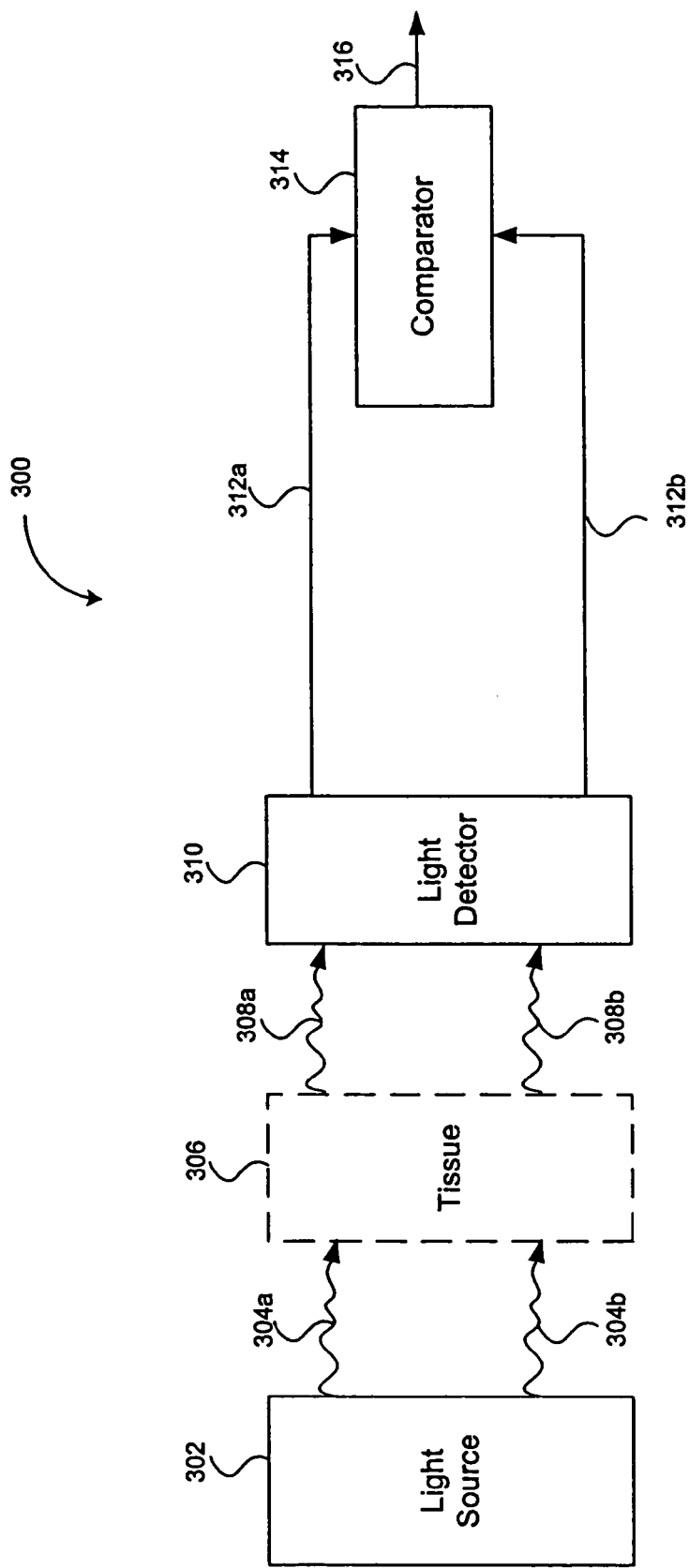
FIG. 3, is a block diagram that illustrates an overview of a photoplethysmography device according to an embodiment of the present invention.

FIG. 3 includes a high level block diagram 300 that provides an overview of an embodiment of the present invention. A light source 302 produces a first transmit light signal 304a and a second transmit light signal 304b. First transmit light signal 304a has a first wavelength $\lambda_1$ that is strongly absorbed by blood, such as near 550 nm or near 600 nm. Second transmit light signal 304b has a wavelength $\lambda_2$ that is absorbed more weakly by blood, such as near 905 nm or near 805 nm. Light signals 304a and 304b are transmitted through and/or reflected by (depending on the embodiment) patient tissue 310, which includes non-blood tissue and blood (i.e., red blood cells). As light signals 304a and 304b travel through patient tissue 310, some of the light energy of each signal is absorbed by blood and some of the light is absorbed by non-blood tissue. However, due to the selected wavelengths, much more energy of first light signal 304a is absorbed by the blood than energy of second light signal 304b. In contrast, the energy of first light signal 304a absorbed by the non-blood tissue and the energy of second light signal 304b absorbed by the non-blood tissue are similar.

The intensity of a transmitted light signals 304a and 304b can be changed by changing the amplitude of the driving current, or for pulsed configurations, the pulse width, frequency, or duty cycle of the current.

A first receive light signal 308a (having the first wavelength $\lambda_1$) and a second receive light signal 308b (having the second wavelength $\lambda_2$) are received at a light detector 310. Light detector 310 outputs a first signal 312a and a second signal 312b. First signal 312a (associated with the first wavelength $\lambda_1$) and second signal 312b (associated with the second wavelength $\lambda_2$) are both representative of volume changes in the non-blood tissue and in blood, with volume changes in the non-blood tissue being primarily due to motion. Since the effective absorption ratios $r_1$ (associated the first wavelength $\lambda_1$) and $r_2$ (associated with the second wavelength $\lambda_2$) are different (as discussed above), the amplitudes of first signal 312a and second signal 312b are different. It is this difference between the two signals 312a and 312b that contains the plethysmography information of interest.

First signal 312a and second signal 312b are compared by a comparator 314. The term "comparator" is used herein to refer to a device (or possibly software) that performs a comparison between two input signals and generates an output based on the results of the comparison. Comparator 314 outputs a difference signal 316 which is equal to second signal 312b subtracted from first signal 312a (or vice versa). Difference signal 316 is a plethysmography signal representative of volume changes in the blood vessels of the patient tissue with motion artifacts reduced and preferably substantially removed or minimized.

Figure 5:
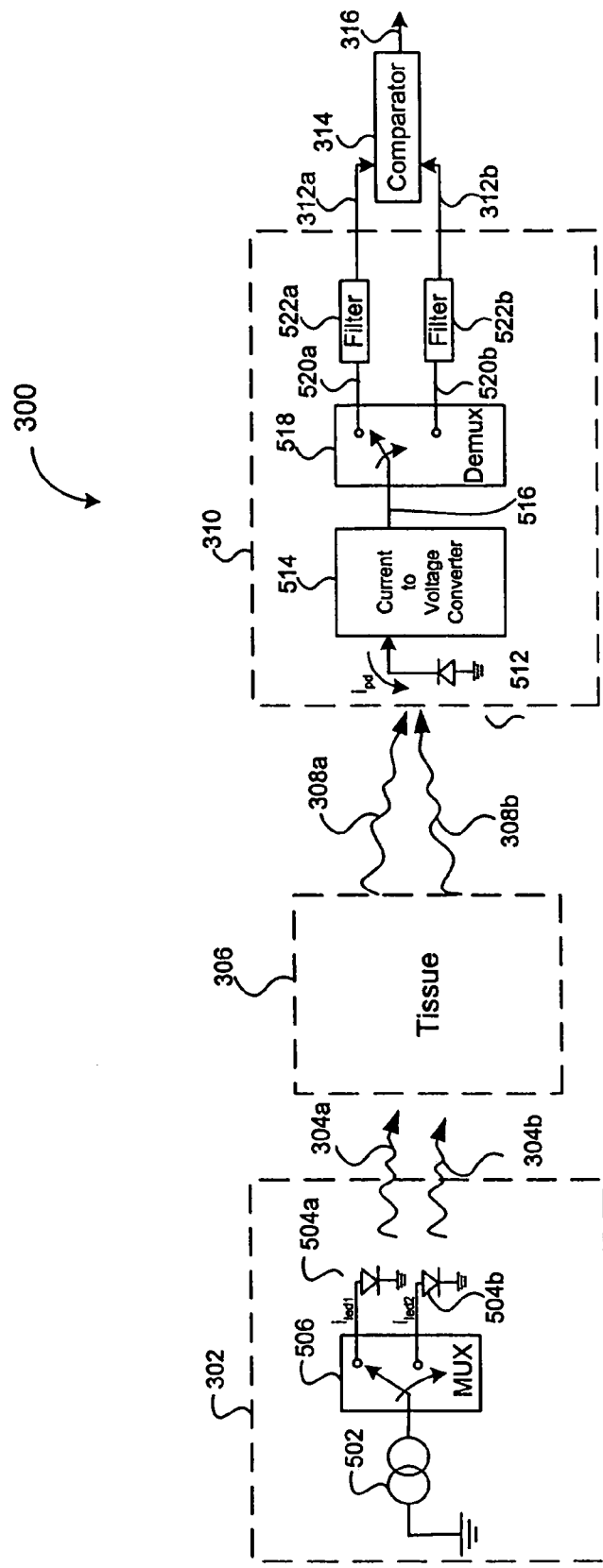
FIG. 5 is a block diagram that illustrates an implementation of the plethysmography device of FIG. 3, according to an embodiment of the present invention.
Figure 9:
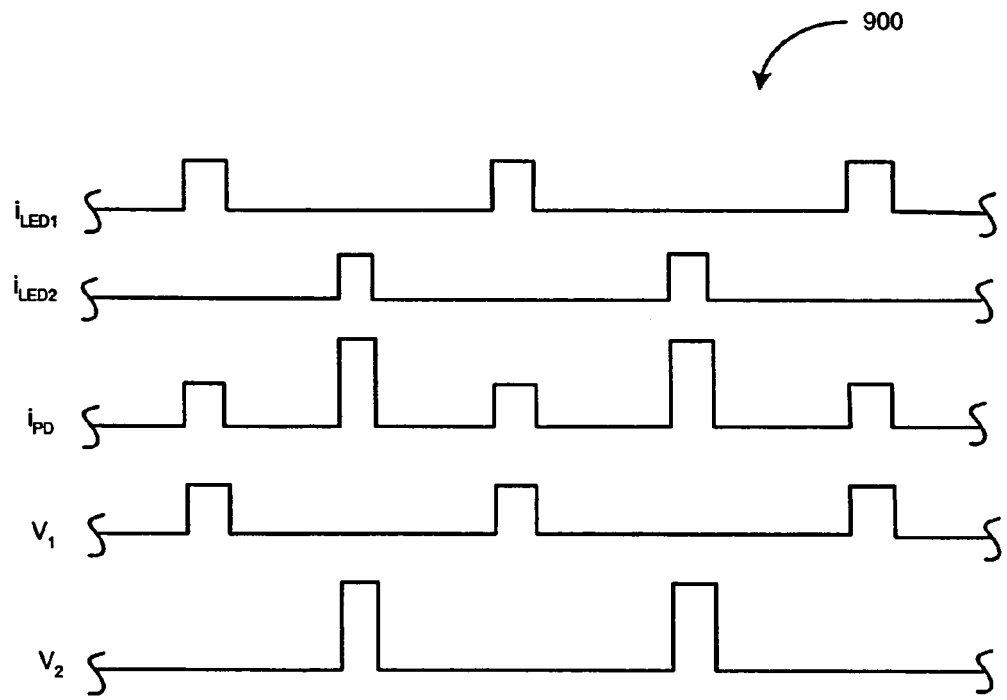
FIG. 9 is a timing diagram that is useful for explaining the operation of the embodiment of FIG. 5.

Additional details of the elements of block diagram 300, according to an embodiment of the present invention, are described with reference to FIG. 5. Referring now to FIG. 5, in accordance with an embodiment of the present invention, light source 302 includes a current source 502, a first LED 504a and a second LED 504b. First LED 504a produces light having a first wavelength below 650 nm (e.g., 600 nm) and second LED 504b produces light having a wavelength above 650 nm (e.g., 805 nm). A multiplexor 506 provides a current signal $i_{LED}$, produced by current source 502, to one of first LED 504a and second LED 504b, in a time multiplexed manner. This produces a first light control signal $i_{LED1}$ that drives first LED 504a and a second light control signal $i_{LED2}$ that drives second LED 504b. FIG. 9 illustrates a timing diagram 900 that is useful for explaining the relationship between first light control signal $i_{LED1}$ and second light control signal $i_{LED2}$. As shown in timing diagram 900, first light control signal $i_{LED1}$ and second light control signal $i_{LED2}$ preferably include non-overlapping pulses. As would be appreciated by one of ordinary skill in the art, two separate pulse generates can be used in place of current source 502 and multiplexor 506.

In accordance with an embodiment of the present invention, light detector 310 includes a photodetector 512 operated in a current sensing photoconductive mode. Photodetector 512 (e.g., a photodiode), produces a photodetector current signal $i_{pd}$ that is fed to a current to voltage converter 514. Current-to-voltage converted 514 converts a photodiode current ($i_{pd}$) to a voltage signal 516. Voltage signal 516 is provided to a demultiplexor 518, which passes voltage signal 516 to a first path 520a or a second path 520b. Demultiplexor 518 operates synchronously with multiplexor 506 so that portions of voltage signal 516 corresponding to first receive light signal 308a (having the first wavelength $\lambda_1$) are passed to first path 520a, and portions of voltage signal 516 corresponding to second receive light signal 308b (having the second wavelength $\lambda_2$) are passed to second path 520b. The portions of voltage signal 516 provided to first path 520a are also referred to, herein, as first voltage signal 520a. The portions of voltage signal 516 provided to second path 520b are also referred to, herein, as second voltage signal 520b.

Referring again to timing diagram 900, in FIG. 9, the relationship is shown between first light control signal $i_{LED1}$, second light control signal $i_{LED2}$ photodiode current signal $i_{pd}$, first voltage signal 520a and second voltage signal 520b. Assume that pulses in first light control signal $i_{LED1}$ and second light control signal $i_{LED2}$ have the same amplitude, as shown in FIG. 9 (which may not always be the case). Notice that amplitudes of pulses (i.e., samples) associated with second voltage signal 520b are greater than pulses associated with first voltage signal 520a, for the time window shown in FIG. 9. This means that more of first transmit light signal 304a (having the first wavelength $\lambda_1$) than second transmit light signal 304b (having the second wavelength $\lambda_2$) was absorbed (by non-blood tissue and blood of patient tissue 306), during this time window.

Referring back to FIG. 5, first voltage signal 520a is provided to a first filter 522a. Similarly, second voltage signal 520b is provided to a second filter 522b. First filter 522a converts the series of pulses of first voltage signal 520a into a continuous waveform, which is first signal 312a. Similarly, second filter 522b converts the series of pulse of second voltage signal 520b into a continuous waveform, which is second signal 312b. Filters 522a and 522b can also perform band pass filtering to filter out noise that is outside the frequency range of interest. In accordance with an embodiment of the present invention, the frequency range of interest is from about 1 Hz to 10 Hz. The noise removed by filters 522a and 522b can include, for example, 60 Hz noise due to power lines and 120 Hz noise due to fluorescent lights. Filters 522a and 522b can also be used to removes motion artifacts that are outside the frequency range of interest. It is the features of the present invention that remove or reduce the motion artifacts that are within the frequency range of interest.

First signal 312a and second signal 312b are provided to comparator 314. As explained above, comparator 314 outputs plethysmography signal 316. Addition details of comparator 314, according to an embodiment of the present invention, are discussed below with reference to FIG. 8.

Additional details of the elements shown in FIG. 5, according to specific embodiments of the present invention, are now described with reference to FIGS. 6, 7 and 8.

Figure 6:
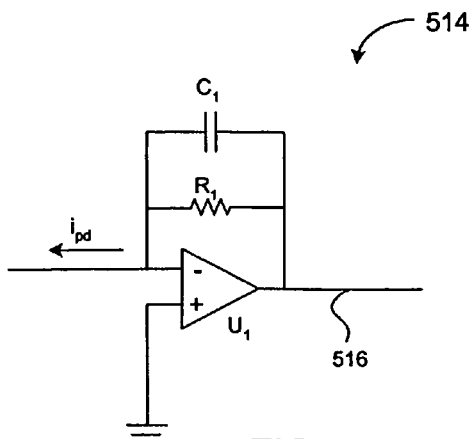
FIG. 6 is a circuit diagram for the current-to-voltage converter of FIG. 5, according to an embodiment of the present invention.

FIG. 6 illustrates a circuit diagram of current-to-voltage converter 514, according to an embodiment of the present invention. In this embodiment, current-to-voltage converter 514 is a transimpedance amplifier that includes a resistor R1, a capacitor C1 and an operational amplifier U1. The transimpedance amplifier performs low pass filtering, anti-alias filtering, and provides gain. The transimpedance amplifier also performs impedance matching that may be necessary where the amplitude of photodiode current signal $i_{pd}$ is not sufficient to drive further components. One of ordinary skill in the art will appreciate that a photodiode can alternatively be operated in a voltage sensing configuration.

One of ordinary skill in the art will appreciate that photodetector 512 can be a photodiode (e.g., an avalanche photodiode), a photo resistor, a photo darlington, a photo transistor, or some other similar detection device, which are all within the spirit and scope of the present invention. One of ordinary skill in the art will also appreciate that other amplifier configurations (e.g., an integrator amplifier, a transistor based amplifier) can be used in place of the transimpedance amplifier shown in FIG. 6. An integrated photodiode/amplifier (e.g., a Burr-Brown OPT101) can also be used. One of ordinary skill in the art will further appreciate that other types of LEDs, or other optical sources, such as, but not limited to laser diodes, lasers and other narrow-spectrum sources can be used to generate the light having the first wavelength and the light having the second wavelength. Broad spectrum sources such as incandescent lamps or tungsten halogen lamps can also be used, with optical filtering performed at the source or detector to provide two effective wavelengths.

Figure 7:
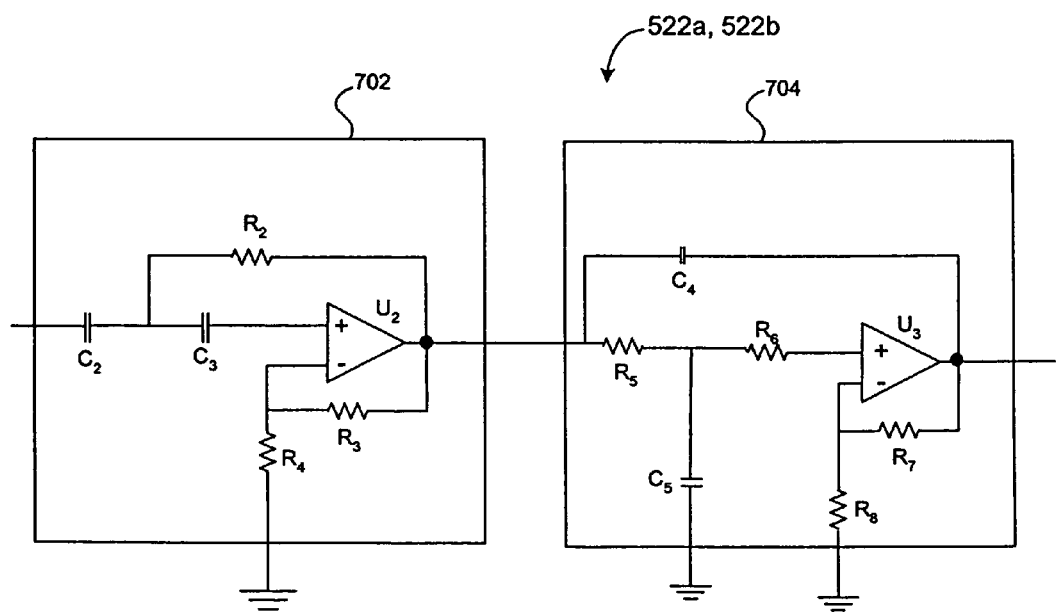
FIG. 7 is a circuit diagram for the filters of FIG. 5, according to an embodiment of the present invention.

FIG. 7 illustrates a circuit diagram that can be used to implement each of filters 522a and 522b, according to an embodiment of the present invention. In this embodiment, filter 522 includes a high pass filter 702 followed by a low pass filter 704, which together form a band pass filter. As shown, low pass filter 702 includes capacitors C2 and C3, resistors R2, R3 and R4, and an operational amplifier U2. High pass filter 704 includes capacitors C4 and C5, resistors R5, R6, R7 and R8, and an operational amplifier U3, as shown. The ratio of R3 to R4 and/or the ratio of R7 to R8 can be adjusted to adjust the effective gain of filter 522. One of ordinary skill in the art will appreciate that use of alternative band pass filters are within the spirit and scope of the present invention.

Figure 8:
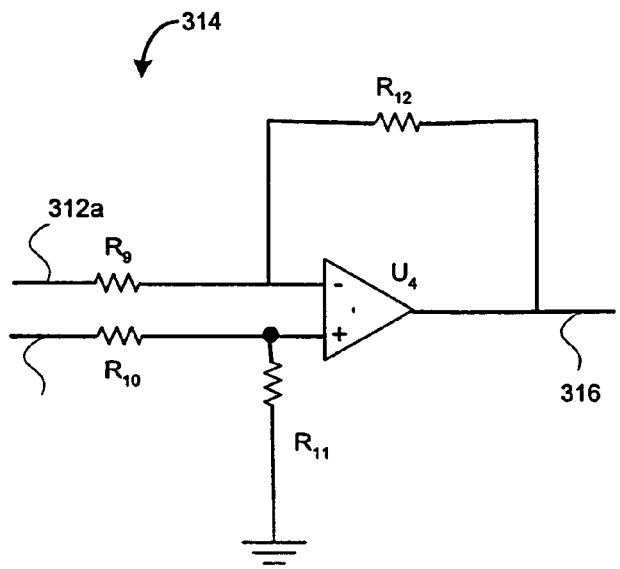
FIG. 8 is a circuit diagram for the comparator of FIG. 5, according to an embodiment of the present invention.

FIG. 8 illustrates a circuit diagram that can be used to implement comparator 314, according to an embodiment of the present invention. In this embodiment, comparator 314 is a differential amplifier that includes resistors R9, R10, R11 and R12, and an operation amplifier U4. The ratio of resistor R11 and R10 can be adjusted to adjust the gain of second signal 312b, and thereby adjust the ratio of first signal 312a to second signal 312b.

Figure 10:
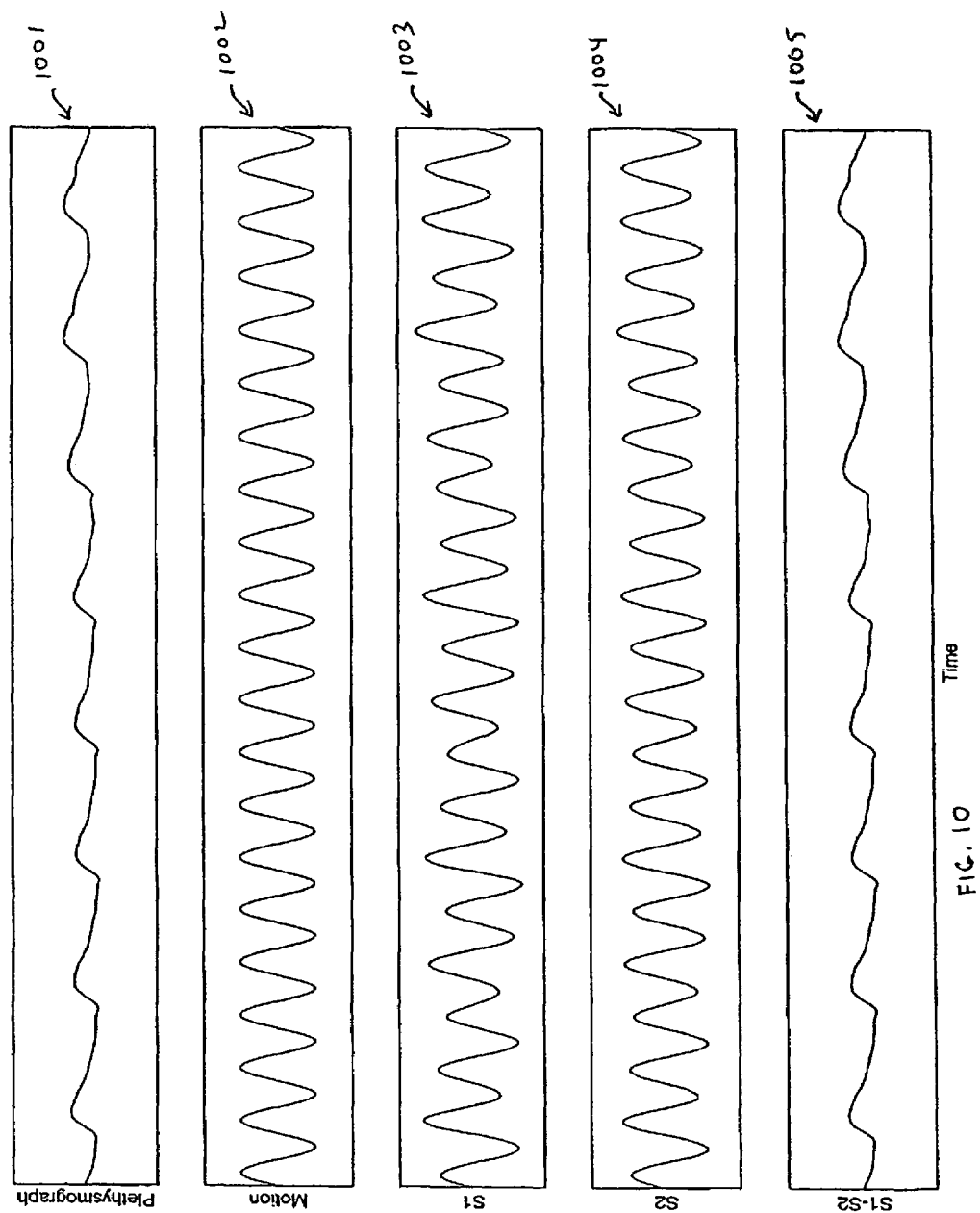
FIG. 10 illustrates exemplary waveforms generated using embodiments of the present invention.

Referring now to FIG. 10, a first waveform 1001 is an exemplary plethysmography signal. Assuming there were no motion artifacts in the non-blood tissue of patient tissue 306, then each of first signal 312a and second signal 312b would resemble this waveform (however, the amplitudes of signal 312a and 312b would be different). Assume that the pulse frequency of this signal is 1.5 Hz, which corresponds to a pulse rate of 90 beats per second. A second waveform 1002 represents exemplary motion artifacts of patient tissue 306. Assume that the frequency of this motion signal is approximately 3.75 Hz. (Of course actual motion artifacts caused by a patient moving and/or breathing would typically have more than one frequency and would have varying amplitude.) A third waveform 1003 represents first signal 312a, which includes both plethysmography information and motion artifacts (due to signal 1002). A fourth waveform 1004 represents second signal 312b, which also includes both plethysmography information and motion artifacts. A fifth waveform 1005, which is a difference between the third waveform 1003 and the fourth waveform 1004, represents desired plethysmography signal 316. Since ratios r1≠r2, the plethysmography waveform 1001 and the motion artifact 1002 are combined in different proportions in the first and second signals 312a, 312b. This allows the plethysmography signal to be recovered when their difference (e.g., first signal 312a−second signal 312b) is taken, while the motion artifact is cancelled.

As explained above, the ratio of $I_{o,2}/I_{o,1}$ (which is the ratio of the intensity of first transmit signal 304a to the intensity of second transmit signal 304b) can be adjusted to minimize the effects of a motion signal (e.g., the effects of signal 1002). This is explained below with reference to FIG. 11. Referring briefly back to FIG. 5, the intensity of first transmit light signal 304a or the intensity of second transmit light signal 304b is can be controlled by adjusting, respectively, the amplitude of $i_{LED1}$ or the amplitude of $i_{LED2}$ (e.g., using a potentiometer). If pulses are being used to drive LEDs 504a and 504b (e.g., as shown in FIG. 9), then average intensities can be controlled by adjusting the amplitude and/or the pulse widths of the pulses. That is, increases in pulse width and/or amplitude increases intensity. Since the desire is to adjust the ratio of intensities, an intensity of one of the transmit light signals 304a, 304b can be kept constant while the other one is adjusted. For example, the intensity of first transmit light signal 304a (i.e., $I_{o,1}$) is kept constant, while the intensity of second transmit light signal 304b (i.e., $I_{o,2}$) is adjusted. The desire is to adjust the intensity ratio until motion artifacts are minimized.

Figure 11:
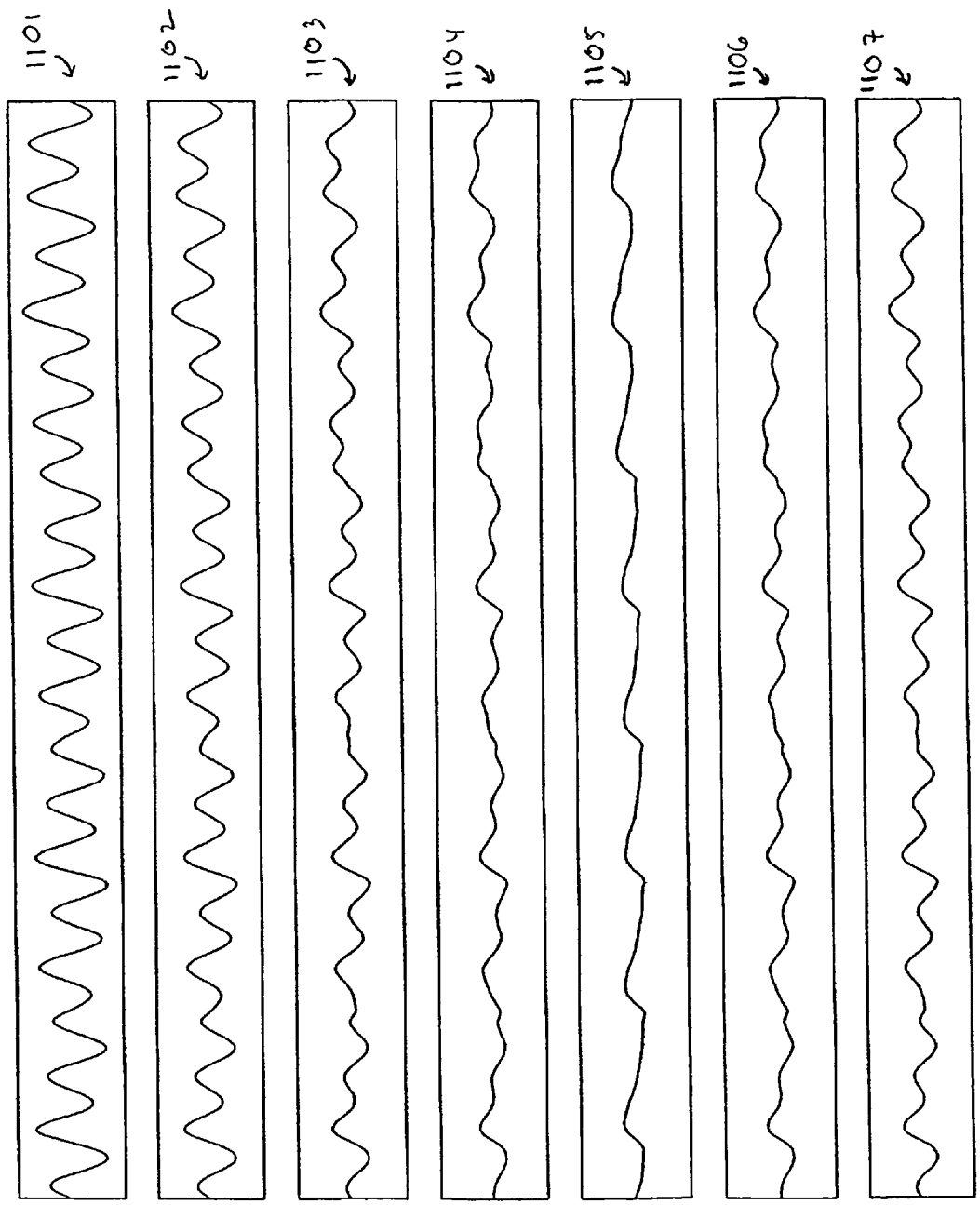
FIG. 11 illustrates various waveforms that are useful for describing how intensity ratios or gain ratios can be adjusted to minimize motion artifacts in accordance with embodiments of the present invention.

Referring now to FIG. 11, each of waveforms 1101-1107 are exemplary plethysmography waveforms 316 (output from comparator 314) with different intensity ratios. As can be observed, the motion artifacts are minimal in waveform 1105. Thus, the intensity ratio that produced this waveform is the preferred ratio. The preferred or substantially optimal ratio can be determined by observing plethysmography signal 316 (e.g., using an appropriate oscilloscope). Alternatively or additionally, a frequency spectral analysis can be performed on plethysmography signal 316. In another embodiment, the variance of plethysmography signal 316 is analyzed and one of the intensities is adjusted (i.e., the ratio is adjusted) until the variance of signal 316 is substantially minimized. Alternatively, the ratio is adjusted until there are a minimum amount of peaks and valleys over a predetermined period of time. These are just a few examples of how the optimal or near optimal intensity ratio can be empirically selected. The optimal ratio can alternatively be theoretically selected using the modified Beer-Lambert law discussed above.

Instead of adjusting the intensity ratio of transmit light signals 304a and 304b, it is equivalent to adjust the gain ratio of signals 312a and 312b. For example, referring to FIGS. 5 and 6, the gain of one of filters 522a and 522b can be adjusted. Alternatively, referring to FIG. 8 (which is an exemplary embodiment of comparator 314), the gain ratio can be adjusted, for example, by adjusting one of resistors R10 or R11.

The above discussed ratios can be adjusted in each plethysmography device such that motion artifacts are minimized for a particular patient. When doing this, a vibrating device (e.g., producing a sinusoidal motion, similar to waveform 1002) can be held against the skin of a patient near the plethysmography device (which may be non-implantable or implantable, as discussed below). Alternatively, and more practical, the ratios are preselected and set such that motion artifacts are minimized for a majority of patients.

Non-Implantable Embodiments

Figure 2A:
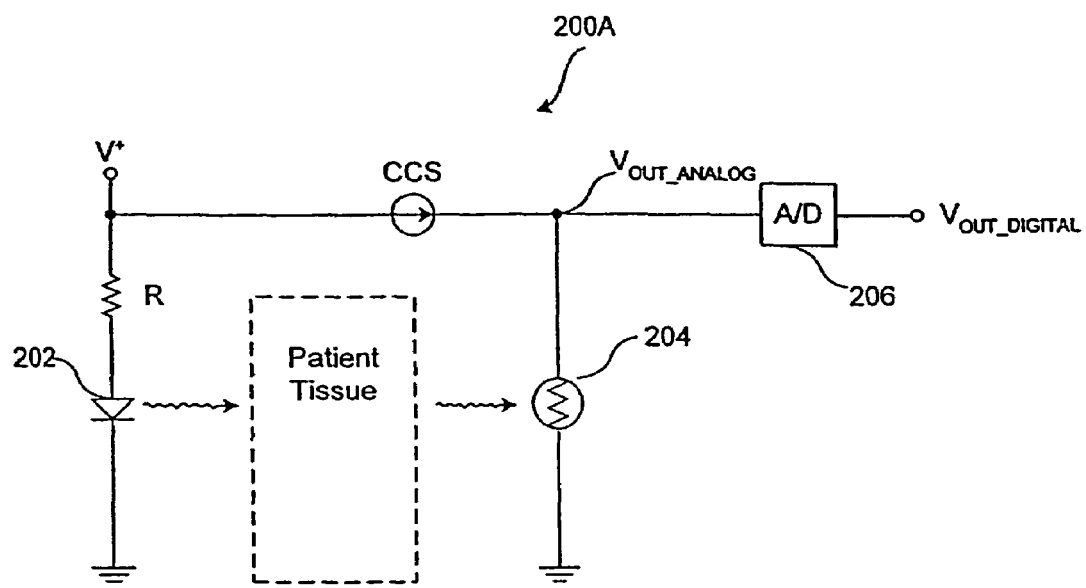
FIG. 2A is a simplified circuit diagram illustrating an exemplary conventional photoplethysmography device.
Figure 2B:
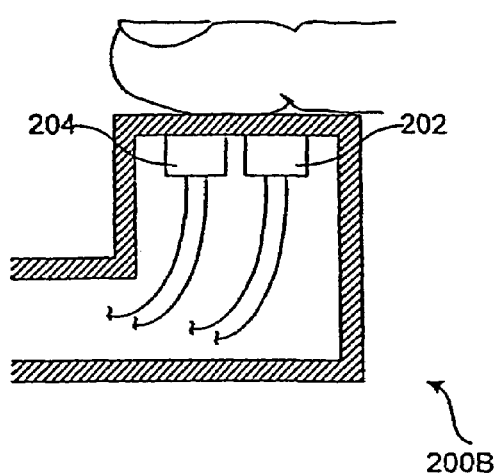
FIG. 2B is a simplified mechanical diagram illustrating a portion of an exemplary conventional photoplethysmography device.

Features of the present invention can be implemented into a non-implantable (i.e., external) device, similar to the one shown in FIG. 2B. The non-implantable devices of the present invention can operate in a transmission or reflection configuration. For example, in a transmission configuration LEDs 504a and 504b would face photodetector 512 so that a human appendage (e.g., a finger, earlobe, hand or foot) can be interposed between the LEDs and detector. In a reflection configuration, LEDs 504a, 504b and photodetector 512 are mounted adjacent to one another and placed against an appendage or against the surface of a patient's body (e.g., against the epidermis of a patient). Accordingly, the phrase "transmitting light through" something (e.g., a human appendage), as used herein, can refer to either a transmission configuration or a reflection configuration.

Implantable Embodiments

Features of the present invention can be incorporated into an implantable device, such as but not limited to an implantable cardioverter defibrillator (ICD) or pacemaker. Alternatively, the features of the present invention can be incorporated into a non-stimulation implantable device whose main purpose is to monitor hemodynamic function. As mentioned above, a problem with optical methods and devices for performing vascular plethysmography is that they are acutely sensitive to sensor and/or tissue motion. With implantable plethysmography devices, such subtle motion may be caused by a patient's walking, or simply breathing. Features of the present invention reduce and preferably minimize the effect of such motion-induced noise.

Exemplary implantable devices of the present invention shall now be described with reference to FIGS. 12A-12C. FIG. 12A shows an implantable device 1200 for monitoring volume changes in blood vessels. As shown, LEDs 504a, 504b and photodetector 512 are incorporated into the housing 1206 of implantable device 1200 (e.g., an ICD, pacemaker, or implantable monitor). LEDs 504a, 504b and photodetector 512 are positioned for a reflected-light configuration. They are preferably placed on the side of device 1200 that, following implantation, faces the interior of the body rather than the surface, and are configured such that light cannot pass directly from LEDs 504a or 504b to photodetector 512. The placement on the side of the device that faces the interior of the body maximizes the signal to noise ratio by 1) directing the signal toward the highly vascularized musculature and 2) shielding the source and detector from ambient light that might enter the body through the skin. In an embodiment, LEDs 504a and 504b and photodetector 512 are placed in a single recess 1215 that is created when the monitor housing 1206 is formed, or, alternatively, machined or cast. An opaque optical barrier 1217 is place between LEDs 504a, 504b and photodetector 512, which ensures that no light passes between them without first interacting with the overlying tissue. Optical barrier 1217 can be made of the same material as device housing 1206, such as titanium or other metal, or can be made from another opaque material such as a polymer. LEDs 504a, 504b and photodetector 512 are physically positioned within recess 1215 such that the amount of reflected light received at photodetector 512 is preferably maximized. In particular, as illustrated in the partial cross section of FIG. 12B, they are angled toward each other with the direction of greatest optical power and sensitivity aligned after reflection from the overlying tissue.

Furthermore, in the preferred embodiment the optical devices have inherent directionality to avoid the need for lenses or other focusing elements, though these are used in alternate embodiments. As illustrated in the cross sections of FIGS. 12B and 12C, recess 1215 has a rounded, concave shape to provide further focusing of stray light. The rounded shape has the added advantage of avoiding low-radius angles which would localize stress when housing 1206 is formed during manufacture. The remaining space in the recess is filled with an epoxy 1210 such that the surface of device 1200 is smooth and flat, thereby minimizing the risk of tissue trauma and infection. The epoxy is preferably of optical quality and transparent at the wavelength of light produced by LEDs 504a, 504b. LEDs 504a, 504b and photodetector 512 are connected via a single feed-through connection 1219 which is hermetically welded to device housing 1206 and connected to the electronic circuit(s) contained within the device 1200. Placing the optical components 502a, 502b and 512 in recess 1215 thereby enhances optical isolation while maintaining hermeticity. Rather than using epoxy 1210, a quartz covering or other equivalent translucent materially can be welded over the recess to hermetically seal the optical components. Further, rather then placing the optical components in a recess, these components can be placed in a separate enclosure that is welded to housing 1206. A feed-through between housing 1206 and the separate enclosure would connect the optical components to the electronic circuit(s) contained within device 1200.

Alternative configurations for the placement of the optical elements (including LEDs 504a, 504b and photodetector 512) can be appreciated from the various embodiments disclosed in U.S. patent application Ser. No. 09/543,214, entitled "Extravascular Hemodynamic Sensor", filed Apr. 5, 2000, which is incorporated herein by reference in its entirety. For example, multiple recesses can be included in housing 1206 for placement of the various optical elements. Alternatively, some or all of the optical elements can be placed in a header 1207 of device 1200. Placement in separate recesses guarantees that all detected light has interacted with the overlying tissue, and avoids the need for an optical barrier 1217 shown in FIGS. 12A-12C. In another embodiment, optical components are placed outside housing 1206 and connected to the internal circuitry via feed-through connector 1219. However, in contrast to the above described embodiment in which a recess is formed in the housing so that the external surface of the device remains flat, in the alternate embodiment no recess is provided. Rather, the device housing 1206 is left flat and the optical components are placed above it. An optical barrier prevents direct transmission of LEDs to the photodetector. In this embodiment, the optical components can be encased in an encapsulant, such as an epoxy, such that the components are mechanically stabilized and separated from the tissue. These are just a few example of how optical components can be positioned. In each of the above described exemplary embodiments, light source 302 and light detector 310 are incorporated into the housing of the implantable device. Further, LEDs 504a, 504b are arranged to transmit light having a first wavelength and light having a second wavelength in a direction generally away from the housing. Photodetector 512 can thereby detect light that has been reflected from tissue within the body of a patient within whom the device is implanted.

Further Embodiments

The above embodiments describe the use of two LEDs 504a, 504b and one photodetector 512. One of the LEDs transmits light at a wavelength less than 650 nm (e.g., 600 nm) and the other transmits light having a wavelength greater than 650 nm (e.g., 805 nm). The same photodetector is used to receive reflected and/or transmitted light having the first frequency and light having the second frequency. The use of time division multiplexing is used to distinguish between or separate the light at the different frequencies, as explained in detail above.

In an alternative embodiment, two LEDs and two photodetectors are used. One of the LEDs transmits light at the first wavelength and the other transmits light at the second wavelength. One of the photodetectors is used to detect the light of the first wavelength, where the other is used to detect light of the second wavelength. Time division multiplexing can be used such that only one of the LEDs at a time is transmitting light and only the appropriate detector is detecting the transmitted light. Alternatively, optical filters (e.g., appropriate thin films) can be placed over the photodetectors so that the appropriate frequencies are detected at each photodetector. In the embodiment using optical filters, both LEDs can be transmitting light at the same time.

In still another embodiment, a broad spectrum source such as a tungsten halogen lamp or a incandescent lamp can be used to transmit light having a broad spectrum of wavelengths including the first and second wavelengths of interest. Two photodetectors are used, each covered by an appropriate optical filter, such that one of the photodetectors detects light having the first wavelength and the other photodetector detects light having the second wavelength.

In the embodiments that use two photodetectors, each photodetector can have its own associated signal conditioning circuitry. For example, referring back to FIG. 5, a current signal $i_{pd}$ produced by one of the photodetectors can drive its own current to voltage converter 514, with the output feeding its own filter 522. That is, the block diagram would look similar to that in FIG. 5, except there would be two separate current-to-voltage converters 514, and no need for demultiplexor 518 because there would be two distinct signal paths. Of course this is just one example of how to implement embodiments where there are two photodetectors.

The plethysmography signal (e.g., signal 316) produced using the present invention can be provided to an analog to digital (A/D) converter and then to a processor (e.g., a microprocessor) for analysis and/or for use in optimization algorithms or for any other purpose. A time domain analysis of the plethysmography signal (e.g., after ND conversion) can be used to calculate pulse amplitude. This can be accomplished by identifying a maximum amplitude, a minimum amplitude, and a difference between the two. An average value for pulse amplitude can also be determined. A frequency domain analysis can be used to calculate spectral power at, for example: the frequency of the heart rate, the frequency of respiration and/or at DC. These are just a few examples of how plethysmography signals produced using embodiments of the present invention can be processed.

All or some of the signal processing performed on the signals produced by photodetector 512 (or any other photodetector) can be performed in the digital domain, while still being within the spirit and scope of the present invention. For example, the signals produced by photodetector 512, or by current-to-voltage converter 514, can be immediately converted into the digital domain and all further processing of these signals (e.g., to determine the differences between detected intensities) can be determined in the digital domain, rather than using analog components. Such digital domain processing can be performed using dedicated digital hardware or on a general purpose processor, such as a microprocessor.

As mentioned above, plethysmography devices might be used, for example, in the cardiac department or intensive care department of a hospital or in a clinic for diagnostic purposes related to vascular surgery. There are numerous applications for which plethysmography signals produced using embodiment of the present invention can be used. Stated another way, there are various types of information one may want to derive from a plethysmography signal. These types of information include, for example, assessment of hemodynamic performance and respiration monitoring. Assessment of hemodynamic performance can include, but is not limited to: pacing parameter optimization (e.g., AV delay, RV-LV delay); optimization of pacing mode (e.g., VDD vs. DDD); arrhythmia discrimination/tailoring anti-arrhythmic therapy; heart failure monitoring; assessment of autonomic tone; capture verification; and sensing optimization. Exemplary pacing parameter optimization algorithms are disclosed in U.S. patent application Ser. No. 09/759,395, entitled "Methods, Systems and Devices for Optimizing Cardiac Pacing Parameters", filed Jan. 12, 2001, and U.S. patent application Ser. No. 09/780,735, entitled "Methods, Systems and Devices for Optimizing Cardiac Pacing Parameters Using Evolutionary Algorithms", filed Feb. 9, 2001, each of which is assigned to the same assignee as the present invention, and each of which is incorporated herein by reference in its entirety. Respiration monitoring can include, but is not limited to: rate responsive pacing; heart failure monitoring (e.g., Cheynes-Stokes respiration, dyspnea, hypopnea); sleep apnea monitoring (e.g., Cheynes-Stokes respiration, dyspnea, hypopnea); and monitoring of pulmonary function (e.g., with asthma patients or chronic obstructive pulmonary disease patients).

Pulse Oximetry Embodiments

In pulse oximetry, the oxygen saturation of a patient's blood is estimated by measuring the absorption of two different wavelengths (e.g., a first wavelength $\lambda_1$ and a second wavelength $\lambda_2$) of light that are transmitted through the tissue of a patient. In conventional pulse oximetry, a statistic or ratio (often referred to as statistic $\omega$, or Ratio R) is determined based on intensities of detected light of a first wavelength $\lambda_1$ and detected light of a second wavelength $\lambda_2$. Conventional formulas for such a statistic $\omega$ or ratio R (collectively referred to hereafter as statistic $\omega$) include $$\omega \approx \frac{\log(I_1) - \log(\langle I_1 \rangle)}{\log(I_2) - \log(\langle I_2 \rangle)} \approx \frac{HPF(I_1)/\langle I_1 \rangle}{HPF(I_2)/\langle I_2 \rangle} \approx \frac{\Delta(I_1)/\langle I_1 \rangle}{\Delta(I_2)/\langle I_2 \rangle}$$

where $I_1$ represents the detected intensity of light having the first wavelength $\lambda_2$, $I_2$ represents the detected intensity of light having the second wavelength $\lambda_2$, $\langle x \rangle$ is used to indicate the average of signal x, HPF(x) is used to indicate signal x after high pass filtering, and $\Delta(x)$ is used to indicate the peak-to-peak amplitude of the pulsatile plethysmography signal. Once statistic $\omega$ is determined, a lookup table or mathematic formula that maps values for statistic $\omega$ with saturation is used to estimate the oxygen saturation. Additional discussions of this statistic or ratio is provided in the following articles, each of which is incorporated herein by reference in its entirety: Coetzee, F. M. and Elghazzawi, Z. "Noise-Resistant Pulse Oximetry Using a Synthetic Reference Signal" *IEEE Transactions on Biomedical Engineering*, Vol. 47. No. 8, August 2000, pages 1018-1026; Yoshiya, I., Simada, Y., and Tanaka, K. "Spectrophotometric Monitoring Of Arterial Oxygen Saturation In the Fingertip," *Medical & Biological Engineering and Computing*, January 1980, pages 27-32; and Flewling, R. "Noninvasive Optical Monitoring," *Biomedical Engineering Handbook*, Chapter 88, CRC Press, 1995, pages 1346-1356.

A problem with determining oxygen saturation using the conventional statistic $\omega$ is that motion artifacts may (and likely will) swamp the measurements of detected light intensities (e.g., $I_1$ and $I_2$), thereby resulting in an inaccurate measure of statistic $\omega$, and thus, an inaccurate estimate of oxygen saturation. Embodiments of the present invention reduce (and preferably minimize) the effects of motion artifacts on detected light intensities using the techniques described above, thereby providing more accurate estimates of oxygen saturation.

The technique described above for minimizing motion artifacts in photoplethysmography combines the signals from two wavelengths to yield a single photoplethysmography signal. As discussed above, the relative intensities are adjusted so that the motion term cancels when the difference between the detected intensities of the first and second wavelengths, $I_1$ and $I_2$, is calculated, leaving $$I_1 - I_2 = I_{0,1} - I_{0,2} + I_b(t)(I_{0,1}K_{r1})\left[\left(\frac{I_{0,2}}{I_{0,1}}\right)\left(\frac{K_{b2}}{K_{b1}}\right) - 1\right].$$

In order to apply this motion rejection technique to pulse oximetry, three wavelengths of light are needed, rather than the two wavelengths used in conventional pulse oximetry. For the purposes of this discussion, assume $I_1$ is the detected intensity of the common 'reference' wavelength that is combined with $I_2$ and $I_3$ to minimize the motion artifacts. In accordance with an embodiment of the present invention, $I_1$ is fixed, and the intensities of $I_2$ and $I_3$ are each adjusted independently so that the effect of motion is minimized in the difference signals $I_1-I_2$ and $I_1-I_3$.

In accordance with embodiments of the present invention, the resulting difference signals are then combined to form a modified statistic $\omega'$, shown below $$\omega' \approx \frac{\log(I_1 - I_2) - \log(\langle I_1 - I_2 \rangle)}{\log(I_1 - I_3) - \log(\langle I_1 - I_3 \rangle)} \approx$$

$$\frac{HPF(I_1 - I_2)/\langle I_1 - I_2 \rangle}{HPF(I_1 - I_3)/\langle I_1 - I_3 \rangle} \approx \frac{\Delta(I_1 - I_2)\langle I_1 - I_2 \rangle}{\Delta(I_1 - I_3)/\langle I_1 - I_3 \rangle}$$

where $I_1$ represents the detected intensity of light having a first wavelength $\lambda_1$, $I_2$ represents the detected intensity of light having a second wavelength $\lambda_2$, $I_3$ represents the detected intensity of light having a third wavelength $\lambda_3$, $\langle x \rangle$ is used to indicate the average of signal x, HPF(x) is used to indicate signal x after high pass filtering, and $\Delta(x)$ is used to indicate the peak-to-peak amplitude of the pulsatile plethysmography signal. The inventor has determined that a cutoff frequency in the range of about 0.1 Hz to about 0.5 Hz is appropriate for the high pass filtering. The advantage of using the modified statistic $\omega'$ is that the effects of motion artifacts on the statistic are reduced (and preferably minimized). In practice, the $\omega'$ statistic would be calculated as indicated in the above equation, or in a way mathematically equivalent to this. Or, a different statistic that similarly operates on the difference signals $I_1-I_2$ and $I_1-I_3$ could be used, while still being within the spirit and scope of the present invention.

In the above equations for the $\omega'$ statistic, the averages of the difference signals (i.e., $\langle I_1-I_2 \rangle$ and $\langle I_1-I_3 \rangle$) are used to normalize the difference signals (i.e., $I_1-I_2$ and $I_1-I_3$). However, these formulas will cause a problem in the rare situation that $I_1=I_2$ or $I_1=I_3$. Accordingly, it may be preferable (although not necessary) to replace $\langle I_1-I_2 \rangle$ simply with $\langle I_2 \rangle$, and to replace $\langle I_1-I_3 \rangle$ simply with $\langle I_3 \rangle$. This leads to the further modified statistic $\omega''$, shown below $$\omega'' \approx \frac{\log(I_1 - I_2) - \log(\langle I_2 \rangle)}{\log(I_1 - I_3) - \log(\langle I_3 \rangle)} \approx \frac{HPF(I_1 - I_2)/\langle I_2 \rangle}{HPF(I_1 - I_3)/\langle I_3 \rangle} \approx \frac{\Delta(I_1 - I_2)\langle I_2 \rangle}{\Delta(I_1 - I_3)/\langle I_3 \rangle}.$$

Figure 13:
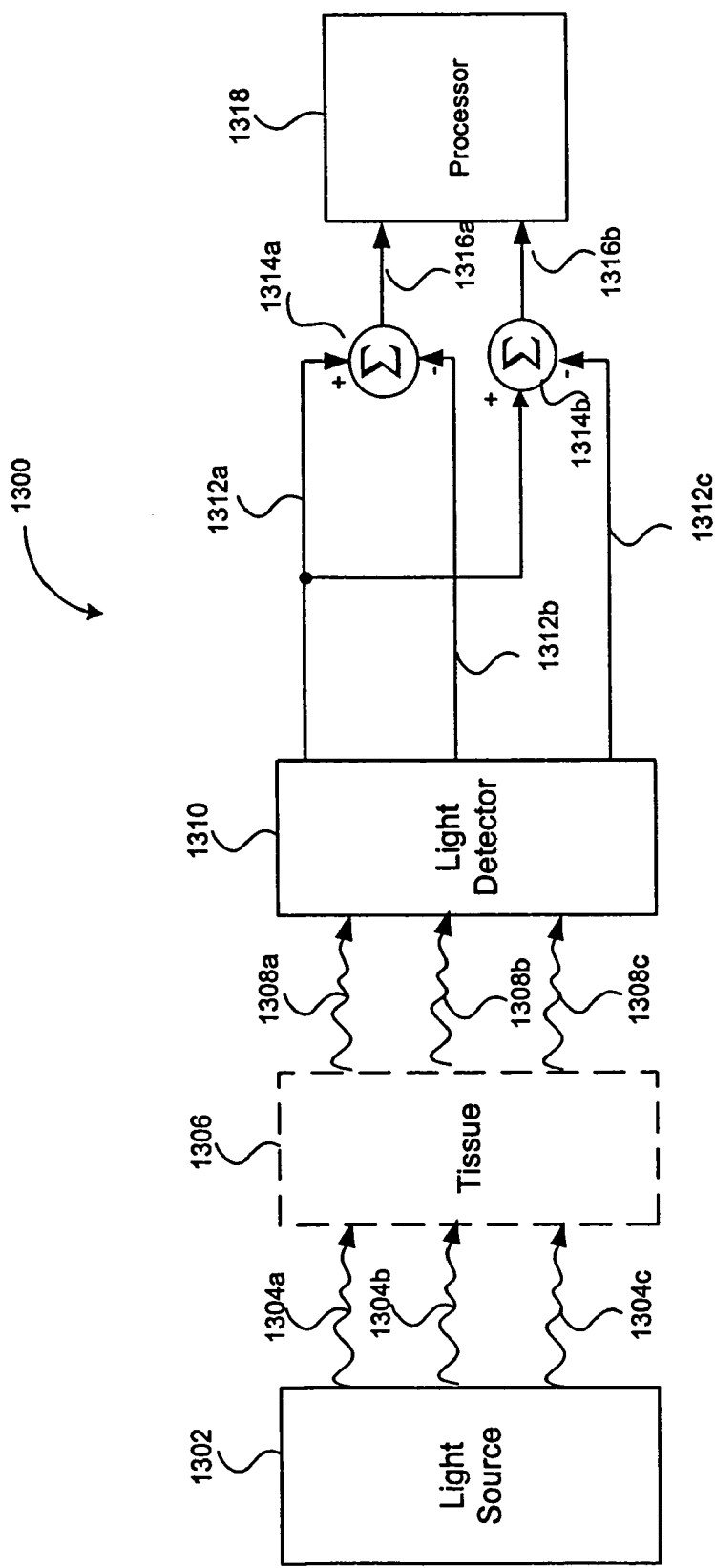
FIG. 13 is a block diagram that illustrates an overview of a pulse oximetry device according to an embodiment of the present invention.

FIG. 13 includes a high level block diagram 1300 that provides an overview of a pulse oximetry embodiment of the present invention, which can be used to estimate oxygen saturation using the above discussed technique for reducing motion artifacts. Additional details of the elements of block diagram 1300, according to an embodiment of the present invention, are described with reference to FIG. 14.

Figure 14:
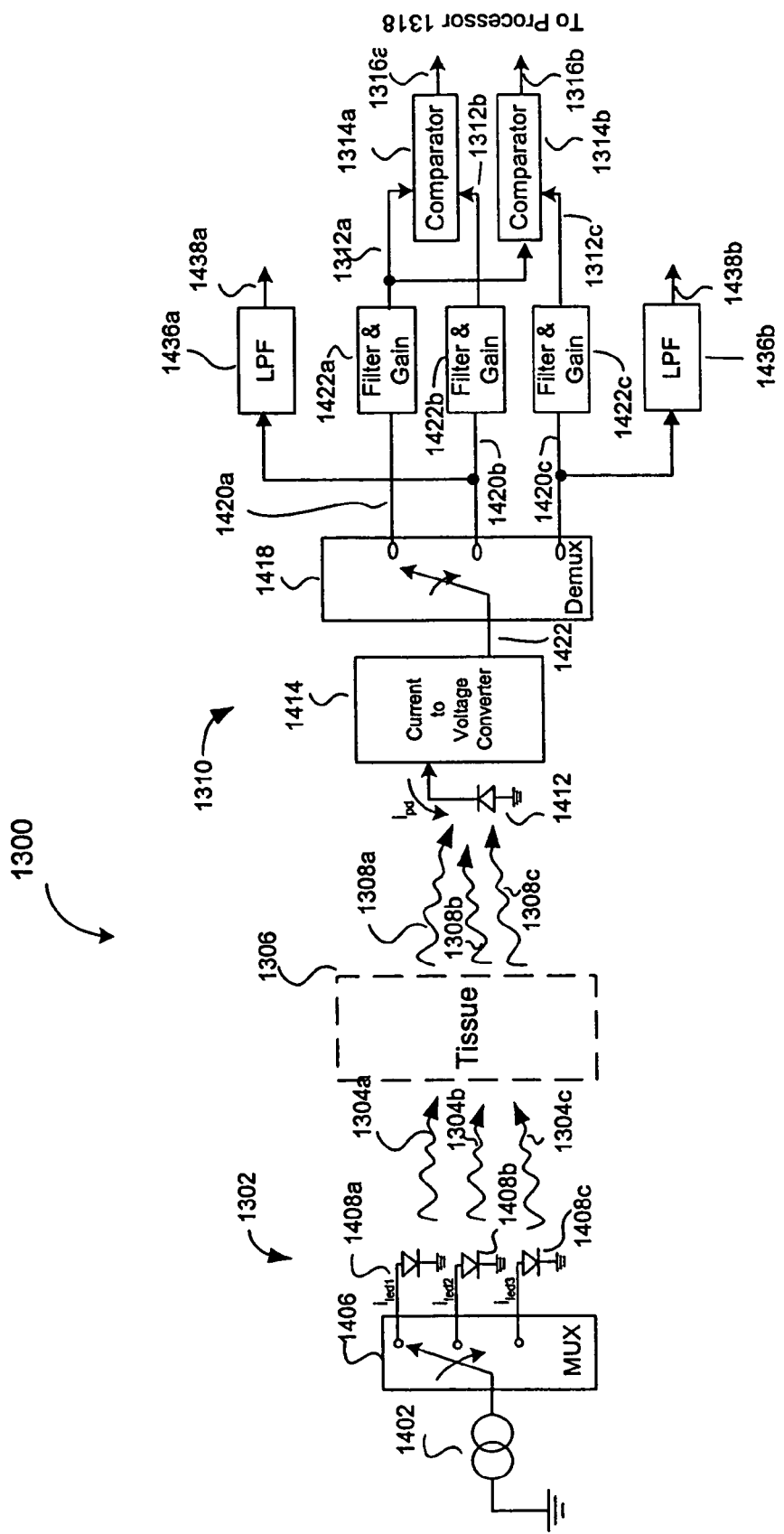
FIG. 14 is a block diagram that illustrates an implementation of the plethysmography device of FIG. 13, according to an embodiment of the present invention.

Referring to FIG. 13, a light source 1302 produces a first transmit light signal 1304a, a second transmit light signal 1304b, and a third transmit light signal 1304c. Light source 1302, as shown in FIG. 14, can include a current source 1402, a multiplexer 1406 and three LEDs 1408a, 1408b and 1408c. First transmit light signal 1304a has a first wavelength $\lambda_1$, second transmit light signal 1304b has a second wavelength $\lambda_2$, and third transmit light signal 1304c has a third wavelength $\lambda_3$. Light signals 1304a, 1304b and 1304c are transmitted through and/or reflected by (depending on the embodiment) patient tissue 1306, which includes non-blood tissue and blood (i.e., red blood cells). As light signals 1304a, 1304b and 1304c travel through patient tissue 1306, some of the light energy of each signal is absorbed by blood and some of the light is absorbed by non-blood tissue.

A first receive light signal 1308a (having the first wavelength $\lambda_1$), a second receive light signal 1308b (having the second wavelength $\lambda_2$), and a third receive light signal 1308c (having the third wavelength $\lambda_3$) are received at a light detector 1310. Light detector 1310 outputs a first signal 1312a (representative of an intensity of first receive light signal 1308a), a second signal 1312b (representative of an intensity of second receive light signal 1308b) and a third signal 1312c (representative of an intensity of third receive light signal 1308c). Referring to FIG. 14, light detector 1310 can include a photodetector 1412, a current to voltage converter 1414, a demultiplexer 1418 and filters 1422, which are substantially similar to photodector 512, current to voltage converter 514, demultiplexer 518 and filters 522, respectively, described above in the discussion of FIGS. 5-7, and thus will not be described again.

First signal 1312a (associated with the first wavelength $\lambda_1$), second signal 1312b (associated with the second wavelength $\lambda_2$) and third signal 1312c (associated with the third wavelength $\lambda_3$) are each representative of volume changes in the non-blood tissue and in blood, with volume changes in the non-blood tissue being primarily due to motion. Since the effective absorption ratios $r_1$ (associated the first wavelength $\lambda_1$), $r_2$ (associated with the second wavelength $\lambda_2$) and $r_3$ (associated with the third wavelength $\lambda_3$) are different (as discussed above), the amplitudes of first signal 1312a, second signal 1312b and third signal 1312c are typically different. Furthermore, the differences in the effective absorption ratios for the different signals causes each signal to contain motion and volume amplitudes in different proportions. By adjusting the amplitude of one signal relative to another (i.e., adjusting the amplitudes of signal 1312b relative to signal 1312a, and signal 1312c relative to signal 1312a) such that the motion amplitudes are equal, the motion component will cancel while the volume component is preserved after the difference is taken. It is the difference between signals 1312a and 1312b and the difference between signals 1312a and 1312c that contain the plethysmography information of interest, which can be used to estimate oxygen saturation with improved accuracy.

First signal 1312a and second signal 1312b are compared by a comparator 1314a. As mentioned above, the term "comparator" is used herein to refer to a device (or possibly software) that performs a comparison between two input signals and generates an output based on the results of the comparison. Thus, this comparison can be done in the analog domain, the digital domain or in software, and accordingly, components such as analog-to-digital converters (not shown) can be used to convert signals to the proper domain.

Comparator 1314a outputs a difference signal 1316a which is equal to second signal 1312b subtracted from first signal 1312a (or vice versa). Difference signal 1316a is a first plethysmography signal representative of volume changes in the blood vessels of the patient tissue with motion artifacts reduced and preferably substantially removed or minimized.

Similarly, first signal 1312a and third signal 1312c are compared by a comparator 1314b. Comparator 1314b outputs a difference signal 1316b which is equal to third signal 1312c subtracted from first signal 1312a (or vice versa). Difference signal 1316b is a second plethysmography signal also representative of volume changes in the blood vessels of the patient tissue with motion artifacts reduced and preferably substantially removed or minimized. First and second plethysmography signals 1316a and 1316b are provided to a processor 1318 (e.g., a microprocessor) which estimates oxygen saturation using these signals in a manner described below. Such estimates of oxygen saturation (as well as the plethysmography signals) can be used for analysis and/or for use in optimization algorithms or for any other purpose.

As mentioned above, first signal 1312a is representative of the intensity of first receive light signal 1308a (i.e., representative of $I_1$), second light signal 1312b is representative of the intensity of the second receive light signal 1308b (i.e., representative of $I_2$), and third light signal 1312c is representative of the intensity of the third receive light signal 1308c (i.e., representative of $I_3$). As just described, first plethysmography signal 1316a is equal to first signal 1312a minus second signal 1312b (or vice versa). Thus, first plethymography signal 1316a is representative of $I_1-I_2$. Similarly, second plethysmography signal 1316b is representative of $I_1-I_3$. Accordingly, first plethysmography signal 1316a and second plethysmography signal 1316b can be used to calculate modified statistics $\omega'$ and $\omega''$, and thus used to estimate oxygen saturation in blood in accordance with embodiments of the present invention. More specifically, first plethysmography signal 1316a and second plethysmography signal 1316b can be used in the above described equations for modified statistics $\omega'$ and $\omega''$.

As discussed above, averages of the difference between intensities of a pair of received light signals (e.g., $<I_1-I_2>$ and $<I_1-I_3>$), or simply the average of intensities (e.g., $<I_2>$ and $<I_3>$), are used to normalize the detected intensities. In accordance with an embodiment of the present invention, each average can be determined using a low pass filter (LPF). For example, referring to FIG. 14, an average of a second voltage signal 1420b can be determined using a LPF 1436a to produce an average signal 1438a (which is the average of second signal 1312b) that is representative of an average intensity of second receive light signal 1308b (i.e., representative of $<I_2>$). Similarly, an average of a third voltage signal 1420c can be determined using a LPF 1436b to produce an average signal 1438b (which is an average of third signal 1312c) that is representative of an average intensity of third receive light signal 1308c (i.e., representative of $<I_3>$). A further low pass filter (not shown) can be used to determine an average intensity of first receive light signal 1308c (i.e., representative of $<I_1>$). Knowing that $<x-y>=<x>-<y>$, the normalization averages $<I_1-I_2>$, $<I_1-I_3>$, or simply $<I_2>$ and $<I_3>$, can be determined using the outputs of the low pass filters. That is, the determined average signals 1438a and 1438b (and also an average of voltage signal 1420a) can be provided to processor 1318 and used to calculate modified statistics $\omega'$ and $\omega''$, and thus used to estimate oxygen saturation in blood in accordance with embodiments of the present invention. It is noted that low pass filters 1436a and 1436b can resemble low pass filter 704 shown in FIG. 7, with the components selected to produce a desired cut off frequency preferably between about 0.1 Hz and 0.5 Hz, although other cutoff frequencies may suffice. One of ordinary skill in the art will appreciate that the use of alternative low pass filters or alternative means for determining an average of a signal are within the spirit and scope of the present invention. For example, one or ordinary skill in the art will also appreciate that processor 1318 can calculate the average signals, thereby eliminating the need for the low pass filters.

In practice, a mapping between arterial blood oxygen saturation and the calculated statistic $\omega'$ or $\omega''$ can be determined empirically in a laboratory. This mapping depends on the details of the light source and detector, the optics, and the geometrical configuration of these components. The empirical relationship can then be modeled using a mathematical function, so that a subsequently measured value of omega is evaluated using the equation to give a predicted arterial oxygen saturation. Alternatively, a sequence of paired values of arterial saturation and the calculated statistic can be recorded in the form of a look up table. Once the mathematical function or look up table is obtained, these are implemented in a device of the present invention to allow oxygen saturation to be determined in a clinical setting. For example, the mathematical function or look up table can be stored in a memory (not shown) accessible by processor 1318.

For reasons similar to those discussed above, selecting any three wavelengths $\lambda_1$, $\lambda_2$, and $\lambda_3$ that satisfy $K_{t2}/K_{b2} \neq K_{t1}K_{b1}$ and $K_{t3}/K_{b3} \neq K_{t1}/K_b$, (where $K_{tn}$ and $K_{bn}$ are, respectively, the effective absorption coefficients of non-blood tissue and blood at the $n^{th}$ wavelength), the source intensities $I_{0,1}$, $I_{0,2}$ and $I_{0,3}$ can be adjusted to minimize the motion signal while preserving the plethysmography signals. Further, to maximize the preserved plethysmography signals the wavelengths are preferably selected so that the difference between $r_1=K_{t1}/K_{b1}$ and $r_2=K_{t2}/K_{b2}$, and the difference between $r_1$ and $r_3=K_{t3}/K_{b3}$, are both relatively large.

In accordance with an embodiment of the present invention, the first wavelength $\lambda_1$ (i.e., the wavelength of first transmit light signal 1304a and first receive light signal 1308a) is selected to be about 805 nm, the second wavelength $\lambda_2$ (i.e., the wavelength of second transmit light signal 1304b and second receive light signal 1308b) is selected to be about 660 nm, and the third wavelength $\lambda_3$ (i.e., the wavelength of third transmit light signal 1304c and third receive light signal 1308c) is selected to be about 905 nm. A rational for selecting such wavelengths is now described. As explained above, the detected intensity associated with $\square_1$ (i.e., $I_1$) is subtracted from the detected intensities associated with each of the other two wavelengths. The amount subtracted is preferably independent of changes in oxygen saturation. As can be appreciated from FIG. 4A, 805 nm is such an isobestic point (a wavelength at which light is absorbed at the same rate by oxygenated and deoxygenated hemoglobin), and thus is a useful wavelength for $\square_1$. The selections of $\square_2$ equal to about 660 nm and $\square_3$ equal to about 905 nm are desirable because there is a strong change in absorbance at the red wavelength (660 nm) and only a modest change in absorbance at the IR wavelength (905 nm) as the oxygen saturation changes. Thus, these two wavelengths are useful in determining the 'color' of the blood, which is representative of the oxygenation state. Finally, as mentioned above, there is a need to ensure that the tissue and blood absorption ratios ($r_1$, $r_2$ and $r_3$) are different at each of the two pairs of wavelengths. Referring to the absorbance spectra of blood and cytochrome aa3 (shown, respectively, in FIG. 4A and FIG. 4D), this appears to be the case since the absorbance of cytochrome aa3 increases more rapidly as the wavelength is shortened from 805 nm than does the absorbance of blood. Similarly, in moving from 805 to longer wavelengths, the absorbance of blood increases while the absorbance of cytochrome aa3 remains flat or even decreases. Note that the absorbance of oxygenated hemoglobin (also know as oxyhemoglobin) dominates since in clinical settings of interest the blood oxygen saturation is greater than 80%. Saturations around this value or lower than it are treated as medical emergencies, and the precise oxygenation saturation level becomes less relevant.

Although the above mentioned wavelengths appear to produce good results, the use of other wavelengths are also within the scope of the present invention.

A ratio $I_{0,2}/I_{0,1}$ (which is the ratio of the intensity of second transmit signal 1304b to the intensity of first transmit signal 1304a) and a ratio $I_{0,3}/I_{0,1}$ (which is the ratio of the intensity of third transmit signal 1304c to first transmit signal 1304b) can be adjusted to minimize the effects of motion, in a manner similar to that described above in connection with FIG. 11. Referring to FIG. 14, keeping the intensity of first light signal 1304a constant, the intensity of second transmit light signal 1304b (or a gain of filter 1422b) can be adjusted until motion artifacts in first plethysmography signal 1316a are minimal, and the intensity of third transmit light signal 1304c (or a gain of filter 1422c) can be adjusted until motion artifacts in second plethysmography signal 1316b are minimal. As explained above, the intensities of transmitted light signals can be changed by changing the amplitude of a driving current, or for pulsed configurations, a pulse width, frequency, or duty cycle of the current. Optimal or near optimal intensity ratios (or gain ratios) can be selected by observing and/or analyzing the first and second plethysmography signals 1316a and 1316b. Such ratios can be adjusted for a particular patient, or can be preselected to minimize motion artifacts for a majority of patients.

The pulse oximetry embodiments of the present invention can be implemented into a non-implantable device, similar to the one shown in FIG. 2B, which can operate in either a transmission or reflection configuration. For example, in a transmission configurations LEDs 1408a, 1408b and 1408c would face photodetector 1412 so that a human appendage can be interposed therebetween. In a reflection configurations, the three LEDs and photodetector would be mounted adjacent to one another so they can be placed against an appendage or against the surface of a patient's body, e.g., against the face of a fetus during peripartum monitoring.

Features of the present invention can also be incorporated into an implantable device that resembles the devices discussed above with reference to FIGS. 12A-12C. However, as can be appreciated from the above description, the implantable pulse oximetry device would require three LEDs, rather the two shown in FIGS. 12A-12C.

The above embodiments describe the use of three LEDs and one photodetector, which is used to receive reflected and/or transmitted light having the first frequency, the second frequency and the third frequency. The use of time division multiplexing is used to distinguish between or separate the light at the different frequencies, as explained in detail above. In an alternative embodiment, three LEDs and three photodetectors are used. Time division multiplexing can be used such that only one of the LEDs at a time is transmitting light and only the appropriate detector is detecting the transmitted light. Alternatively, optical filters (e.g., appropriate thin films) can be placed over the photodetectors so that the appropriate frequencies are detected at each photodetector. In the embodiment using optical filters, all LEDs can be transmitting light at the same time.

In still another embodiment, a broad spectrum source such as a tungsten halogen lamp or a incandescent lamp can be used to transmit light having a broad spectrum of wavelengths including the first, second and third wavelengths of interest. Three photodetectors are used, each covered by an appropriate optical filter, such that one of the photodetectors detects light having the first wavelength, another detects light having the second wavelength, and the other detects light having the third wavelength.

All or some of the signal processing performed on the signals produced by photodetector 1412 (or any other photodetector) can be performed in the digital domain, while still being within the spirit and scope of the present invention. For example, the signals produced by photodetector 1412, or by current-to-voltage converter 1414, can be immediately converted into the digital domain (e.g., using an analog-to-digital converter) and all further processing of these signals (e.g., to determine the differences between detected intensities) can be determined in the digital domain, rather than using analog components. Such digital domain processing can be performed using dedicated digital hardware or on a general purpose processor (e.g., processor 1318), such as a microprocessor.

As mentioned above, pulse oximetry devices might be used, for example, in the cardiac department or intensive care department of a hospital or in a clinic for diagnostic purposes. There are numerous applications for which estimates of blood oxygen saturation produced using embodiment of the present invention can be used. Exemplary applications include, as mentioned above, monitoring and assessment of heart failure, sleep apnea, and pulmonary function.

The previous description of the preferred embodiments is provided to enable a person skilled in the art to make or use the present invention. While the invention has been particularly shown and described with reference to preferred embodiments thereof, it will be understood by those skilled in the art that various changes in form and details may be made therein without departing from the spirit and scope of the invention.

What is claimed is:

1. A method for reducing effects of motion when measuring blood oxygen saturation, comprising the following steps of:
   (a) transmitting light having a first wavelength, light having a second wavelength and light having a third wavelength through body tissue;
   (b) receiving a portion of the light having the first wavelength, a portion of the light having the second wavelength and a portion of the light having the third wavelength;
   (c) producing a first signal based on the received portion of light having the first wavelength, a second signal based on the received portion of light having the second wavelength, and a third signal based on the received portion of light having the third wavelength;
   (d) determining a difference between the second signal and the first signal to produce a first plethysmography signal, and a difference between the third signal and the first signal to produce a second plethysmography signal;
      adjusting a first ratio between an intensity of the light having the first wavelength and an intensity of the light having the second wavelength to thereby reduce motion artifacts associated with the first plethysmography signal; and
      adjusting a second ratio between an intensity of the light having the first wavelength and an intensity of the light having the third wavelength to thereby reduce motion artifacts associated with the second plethysmography signal; and
   (e) estimating blood oxygen saturation using the first and second plethysmography signals, wherein the estimating is performed using a processor.

2. The method of claim 1, wherein an intensity of the light having the first wavelength is kept constant while
   the intensity of the light having the second wavelength is adjusted to substantially minimize the motion artifacts associated with the first plethysmography signal, and
   the intensity of the light having the third wavelength is adjusted to substantially minimize motion artifacts associated with the second plethysmography signal.

3. The method of claim 1, wherein intensities of the light having the first wavelength, the light having the second wavelength, and the light having the third wavelengths are selected to substantially minimize motion artifacts in the first plethysmography signal and motion artifacts in the second plethysmography signal.

4. The method of claim 1, wherein step (a) comprises transmitting the light having the first wavelength, the light having the second wavelength and the light having the third wavelength through a patient's finger, earlobe, foot or hand.

5. The method of claim 1, wherein step (a) comprises transmitting the light having the first wavelength, the light having the second wavelength and the light having the third wavelength from a light source implanted within a patient's body.

6. The method of claim 1, wherein step (a) comprises transmitting the light having the first wavelength, the light having the second wavelength and the light having the third wavelength from a light source against or in close proximity to an epidermis of a patient.

7. The method of claim 1, wherein the first wavelength is about 805 nm, the second wavelength is about 660 nm and the third wavelength is about 905 nm.

8. The method of claim 1, further comprising the step of:
determining an average of the second signal and an average of the third signal; and
using the averages in step (e) when estimating the blood oxygen saturation.

9. The method of claim 1, further comprising the step of:
determining an average of the first signal, an average of the second signal, and an average of the third signal; and
using the averages in step (e) when estimating the blood oxygen saturation.

10. The method of claim 1, wherein step (e) includes:
determining a statistic using the first and second plethysmography signals, and
estimating the blood oxygen saturation based on the statistic.

11. A method for reducing effects of motion when measuring blood oxygen saturation, comprising the following steps of:
(a) transmitting light having a first wavelength, light having a second wavelength and light having a third wavelength through body tissue;
(b) receiving a portion of the light having the first wavelength, a portion of the light having the second wavelength and a portion of the light having the third wavelength;
(c) producing a first signal based on the received portion of light having the first wavelength, a second signal based on the received portion of light having the second wavelength, and a third signal based on the received portion of light having the third wavelength;
(d) determining a difference between the second signal and the first signal to produce a first plethysmography signal, and a difference between the third signal and the first signal to produce a second plethysmography signal;
adjusting a first ratio between a gain of the first signal and a gain of the second signal to thereby reduce motion artifacts associated with the first plethysmography signal; and
adjusting a second ratio between a gain of the first signal and a gain of the third signal to thereby reduce motion artifacts associated with the second plethysmography signal; and
(e) estimating blood oxygen saturation using the first and second plethysmography signals, wherein the estimating is performed using a processor.

12. The method of claim 11, wherein the gain of the first signal is kept constant while
the gain of the second signal is adjusted to substantially minimize motion artifacts associated with the first plethysmography signal, and
the gain of the third signal is adjusted to substantially minimize motion artifacts associated with the second plethysmography signal.

13. A device for measuring blood oxygen saturation, comprising:
a light source to transmit light having a first wavelength, light having a second wavelength and light having a third wavelength through body tissue;
a light detector to receive a portion of the light having the first wavelength, a portion of the light having the second wavelength, and a portion of the light having the third wavelength, and to produce a first signal, based on the received portion of light having the first wavelength, a second signal, based on the received portion of light having the second wavelength, and a third signal, based on the received portion of the light having the third wavelength;
a first comparator to subtract one of the first and second signals from the other to produce a first plethysmography signal;
a second comparator to subtract one of the first and third signals from the other to produce a second plethysmography signal;
means for adjusting one or more of the following ratios, to thereby reduce motion artifacts associated with at least one of the first and second plethysmography signals: a ratio between an intensity of the light having the first wavelength and an intensity of the light having the second wavelength, a ratio between an intensity of the light having the first wavelength and an intensity of the light having the third wavelength, a ratio between a gain of the first signal and a gain of the second signal, and a ratio between a gain of the first signal and a gain of the third signal; and
means for estimating the blood oxygen saturation using the first and second plethysmography signals.

14. The device of claim 13, wherein the body tissue is within a human appendage of a patient.

15. The device of claim 13, wherein the body tissue is located below the epidermis of a patient.

16. The device of claim 13, wherein the first wavelength is about 805 nm, the second wavelength is about 660 nm and the third wavelength is about 905 nm.

17. The device of claim 13, wherein the light source comprises:
a first light emitting diode to produce the light having the first wavelength;
a second light emitting diode to produce the light having the second wavelength; and
a third light emitting diode to produce the light having the third wavelength.

18. The device of claim 13, wherein the light source comprises:
a first laser diode to produce the light having the first wavelength;
a second laser diode to produce the light having the second wavelength; and
a third laser diode to produce the light having the third wavelength.

19. The device of claim 13, wherein the light source comprises a lamp to produce a range of wavelengths including the light having the first wavelength, light having the second wavelength, and light having the third wavelength.

20. The device of claim 19, wherein the lamp comprises one of an incandescent lamp and a tungsten halogen lamp.

21. The device of claim 19, wherein the light detector comprises:
a first photodetector covered by a first optical filter that selectively passes light having the first wavelength;

a second photodetector covered by a second optical filter that selectively passes light having the second wavelength; and a third photodetector covered by a third optical filter that selectively passes light having the third wavelength.

22. The device of claim 13, wherein the light detector comprises a first photodetector to receive the portion of the light having the first wavelength, a second photodetector to receive the portion of the light having the second wavelength, and a third photodetector to receive the portion of the light having the third wavelength.

23. The device of claim 13, wherein the light detector includes a photodetector to receive the first portion of light having the first wavelength, the second portion of light having the second wavelength and the third portion of light having the third wavelength.

24. The device of claim 23, wherein the light detector includes a demultiplexor to separate a first portion of a voltage signal representative of the first portion of light having the first wavelength from a second portion of the voltage signal representative of the second portion of light having the second wavelength and a third portion of the voltage signal representative of the third portion of light having the third wavelength.

25. The device of claim 24, wherein the light detector further includes:

a first bandpass filter to produce the first signal from the first portion of the voltage signal;

a second bandpass filter to produce the second signal from the second portion of the voltage signal; and a third bandpass filter to produce the third signal from the third portion of the voltage signal.

26. The device of claim 13, wherein each comparator comprises a differential amplifier.

27. The device of claim 13, wherein the means for estimating blood oxygen saturation comprises a processor.

28. The device of claim 13, further comprising:

means for determining an average of the second signal; and means for determining an average of the third signal;

wherein the means for estimating blood oxygen saturation also uses the averages when estimating blood oxygen saturation.

29. The device of claim 28, wherein each means for determining an average comprises a low pass filter.

30. The device of claim 13, further comprising:

means for determining an average of the first signal;

means for determining an average of the second signal; and means for determining an average of the third signal;

wherein the means for estimating blood oxygen saturation also uses the averages when estimating blood oxygen saturation.

31. The device of claim 30, wherein each means for determining an average comprises a low pass filter.

32. The device of claim 13, wherein the light source and the light detector are configured, with respect to one another, in a transmission configuration.

33. The device of claim 13, wherein the light source and the light detector are configured, with respect to one another, in a reflection configuration.

* * * * *